United States Patent [19]

Hof

[11] 4,408,282
[45] Oct. 4, 1983

[54] AC RESISTANCE MEASURING INSTRUMENT

[75] Inventor: Peter J. Hof, Richland, Wash.

[73] Assignee: The United States of America as represented by the U.S. Department of Energy, Washington, D.C.

[21] Appl. No.: 256,372

[22] Filed: Apr. 22, 1981

[51] Int. Cl.³ .......................................... G01R 27/00
[52] U.S. Cl. .................................. 364/482; 364/571; 324/57 R; 324/65 R
[58] Field of Search ............... 364/480, 481, 482, 483, 364/550, 551, 571; 324/57 R, 59, 62, 64, 65 R, DIG. 1

[56] References Cited

U.S. PATENT DOCUMENTS

| | | | |
|---|---|---|---|
| 4,196,475 | 4/1980 | Hall | 364/482 |
| 4,214,311 | 7/1980 | Nakashima et al. | 324/62 |
| 4,264,860 | 4/1981 | Thebault | 324/62 |

Primary Examiner—Gary Chin
Attorney, Agent, or Firm—Walter L. Rees; Jeannette M. Walder; Richard G. Besha

[57] ABSTRACT

An auto-ranging AC resistance measuring instrument for remote measurement of the resistance of an electrical device or circuit connected to the instrument includes a signal generator which generates an AC excitation signal for application to a load, including the device and the transmission line, a monitoring circuit which provides a digitally encoded signal representing the voltage across the load, and a microprocessor which operates under program control to provide an auto-ranging function by which range resistance is connected in circuit with the load to limit the load voltage to an acceptable range for the instrument, and an auto-compensating function by which compensating capacitance is connected in shunt with the range resistance to compensate for the effects of line capacitance. After the auto-ranging and auto-compensation functions are complete, the microprocessor calculates the resistance of the load from the selected range resistance, the excitation signal, and the load voltage signal, and displays of the measured resistance on a digital display of the instrument.

16 Claims, 8 Drawing Figures

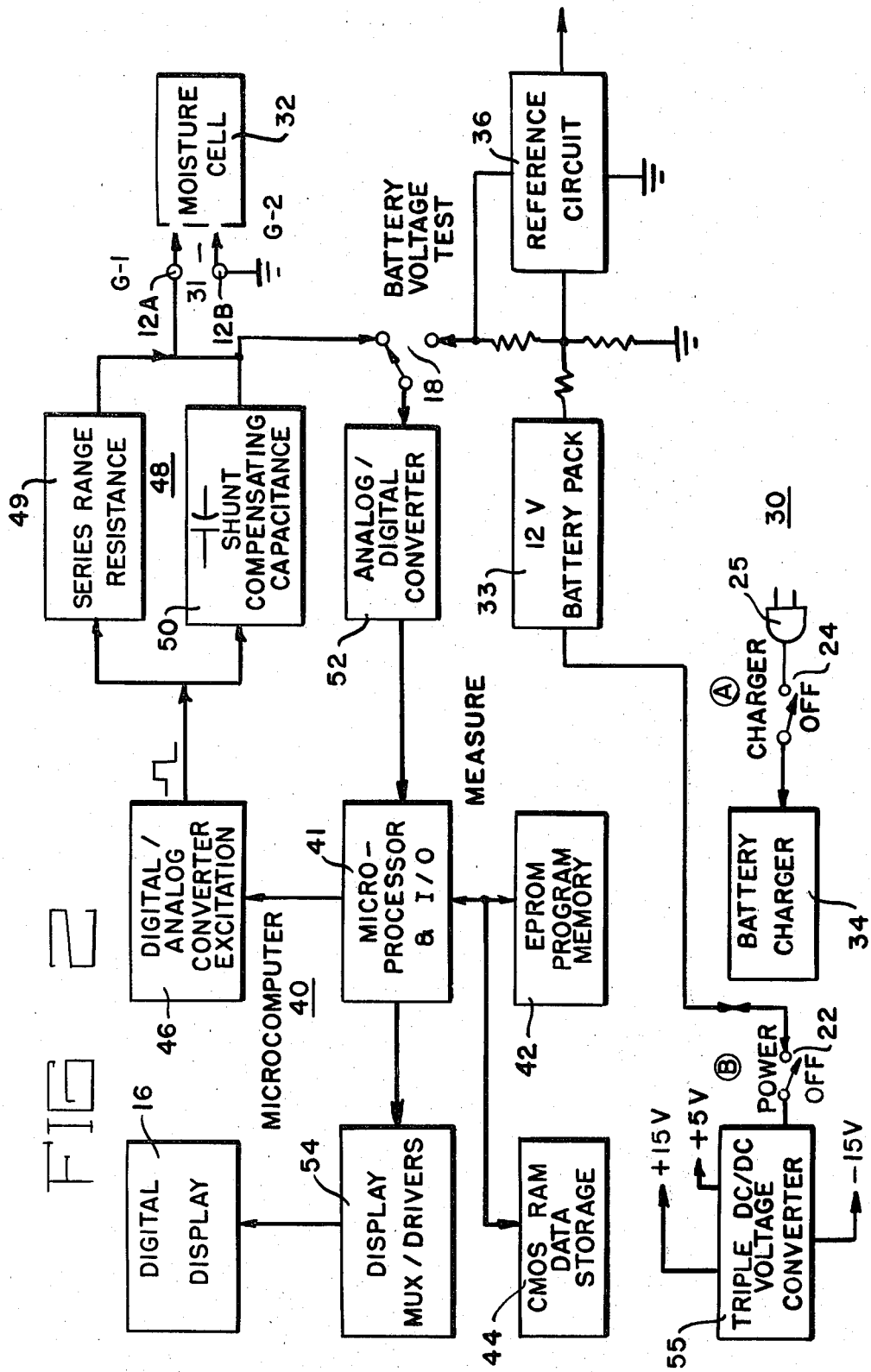

AC RESISTANCE MEASURING INSTRUMENT

CONTRACTUAL ORIGIN OF THE INVENTION

The United States Government has rights in this invention pursuant to Contract No. EY-76-C-06-1830 between the U.S. Department of Energy and Battelle Pacific Northwest Laboratories.

BACKGROUND OF THE INVENTION

This invention relates to measuring instruments and more particularly to an instrument for remote measuring of AC resistance over long lines.

The control and study of large irrigation systems involves monitoring changes in moisture content of soil in a field under test. This is generally accomplished by using soil moisture test cells which are located at different points in the field under test. The test cells behave as varying resistance in series with varying capacitance with a change in soil moisture, and variations in soil moisture content is monitored by periodically measuring the impedance, or AC resistance, of each test cell. The test cells are comprised of two stainless steel grid cylinders, one centered inside the other, forming plates to which an AC excitation signal is applied for measuring the impedance. The cost of manually connecting an instrument to individual moisture cells at each test location is prohibitive when surveying large areas. Moreover, measuring the resistance of the test cells on an individual basis requires that a technician walk through the field under test, and it is possible that other test arrangements may be disturbed, adversely affecting the reliability of the test results.

Measuring instruments have been proposed for the purpose of remote measuring of the AC resistance of soil moisture test cells. One such instrument employed a balanced bridge technique to compensate for line impedance. However, both resistance and capacitance balancing were required to achieve a null, and false nulls were possible when the approximate capacitance was not known. Another instrument, designed to compensate for the influence of excitation applitude, series resistance and excitation frequency, employed a technique for rectifying and averaging measured AC resistance. However, this instrument provided no compensation for line capacitance. Neither one of these instruments performed entirely satisfactory.

Therefore a need exists for a portable instrument capable of measuring AC resistance over long lines, typically hundreds of feet in length, and providing reliable readings of the resistance measured.

SUMMARY OF THE INVENTION

The present invention provides an auto-ranging AC resistance measuring instrument with line capacitance compensation for measuring the impedance, or AC resistance, of a device, or circuit, over long lines, which may be hundreds of feet in length, and providing a numerical display of the impedance measured. The instrument is a battery-operated, portable unit, suitable for field use.

The measuring instrument comprises a signal generating means for generating an AC excitation signal which is applied to the device through the line which connects the device to the instrument. A monitoring circuit means provides an output signal corresponding to the voltage across the load, including the line and the device, and a signal processing means samples and averages this output over a period of time to provide an output which is indicative of the impedance, or AC resistance, of the device and causes the value of the resistance measured to be displayed on a numerical display.

In accordance with the invention, which is described with reference to measurement of the impedance of soil test moisture cells, during each measurement cycle, the signal processing means provides an auto-ranging function by controlling a range resistance network to connect resistance in series with the load as a function of the load voltage measured. The value of the series range resistance is selected, automatically, to maintain the amplitude of the load voltage within a desired range. The signal processing means also controls a capacitance compensating network to connect capacitance in parallel with the series range resistance to enable the line capacitance to be "pre-charged" so as to minimize distortion of the excitation signal. A symmetrical square wave excitation signal is used to reduce the accuracy requirements of the compensating capacitance.

In providing the auto-compensating function, the signal processing means, by way of the monitoring circuit means, monitors the wave shape of the load voltage and causes binary weighted capacitors to be added incrementally, in parallel with the range resistance until the slope of the load voltage wave form becomes zero or slightly negative, indicative that line compensation has been achieved. One advantage of this technique is that only compensating capacitance need be inserted in parallel with the series range resistance, a technique that is simpler than standard bridge "null" techniques and makes auto ranging and auto-compensating more economically feasible.

In accordance with a feature of the invention, the signal processing means comprises a microprocessor operating under program control to enable the signal generating means to generate its excitation signal, to analyze the signal output of the monitoring circuit means and to control the range resistance and compensating capacitance networks to achieve the desired compensation.

During each measurement operation, the first of five ranges is selected and an excitation signal is applied to the moisture cell under test. The values of a plurality of samples are averaged, and the last value is compared with an upper limit established for range one. If the measured value is below this limit, the averaged data are displayed. However, if the measured value is above this limit, then, the next higher range, range two, is selected by increasing the range resistance and another measurement cycle is initiated.

If the measured value exceeds a second, higher limit established for range two, range three is selected, the range resistance is increased, and a further measurement cycle is initiated, and so on, until the measured impedance is below the upper limit for the selected range.

Ranges one and two are used for relatively low impedances 50K ohms or less, where line capacitance is not a factor in measuring the impedance of the soil moisture cell under test. For higher impedances, i.e. when ranges three through five are used, line capacitance becomes a factor in the measured reading, causing distortion of the square wave signal applied to the load. Capacitance is added in parallel with the range resistance, a few hundred picofarads at a time, until the load voltage waveform once again approximates the waveform of the square wave excitation signal, indicating compensation has been achieved. The load voltage is sampled near its leading and trailing edges in both positive and negative half cycles, thereby offsetting any errors that may be introduced by the electronic circuitry or moisture cell polarization.

In accordance with a further feature of the invention, the battery voltage is automatically tested at the start of each measurement cycle. If the battery voltage becomes less than, or greater than, selected high and low limits, the measurement cycle is terminated, and a suitable indication is displayed on the display unit.

BRIEF DESCRIPTION OF THE DRAWINGS

FIG. 2 is a block diagram of the measuring instrument shown in FIG. 1;

DESCRIPTION OF THE PREFERRED EMBODIMENT

Figure 1:
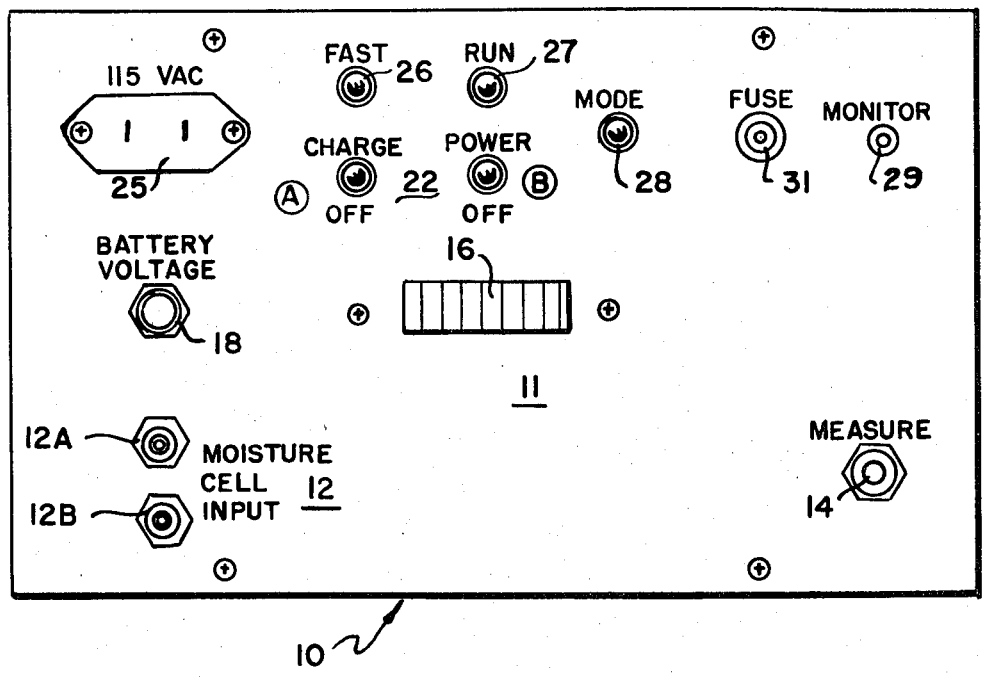
FIG. 1 is a view of the AC resistance measuring instrument provided by the present invention.

Referring to FIG. 1, the impedance or AC resistance measuring instrument is a portable, self-contained, battery operated unit. The instrument includes a housing 10 which encloses the circuits of the instrument as well as a rechargable battery pack which energizes the circuits. A front panel 11 of the instrument mounts a pair of terminals 12 by which a device or circuit, the impedance of which is to be measured, is connected to the instrument. A push-button switch 14, when operated, enables the circuits of the instrument to measure the impedance of the device or circuit connected to terminals 12, and display the measured value on a digital display 16 located on the panel 11. A run indicator 27 flashes periodically while the readout 16 is blanked during a pending measurement.

For purposes of illustration, the measuring instrument is described with reference to an application for measuring the impedance or AC resistance of soil moisture cells which serve as moisture sensors in the control and/or study of a large irrigation system. The moisture test cells are commercially available, or easily constructed and accordingly are not shown in detail. One example of a moisture test cell suitable for this purpose comprises two stainless steel grid cylinders, one centered inside the other. The cylinders are separated by gypsum which absorbs moisture at the same rate as do plants. The moisture cell has two terminals each connected to a different one of the grid cylinders. The moisture cells are set in the ground at various depths from six inches to a few feet down. Each soil moisture cell behaves primarily as a resistance in series with a capacitance, both of which vary in accordance with changes in the amount of moisture in the soil.

To simplify the description, the instrument is described with reference to an application for measuring the impedance of a single moisture cell represented by block 32 in FIG. 2. In use, however, the instrument measures the impedances of a large number of such test cells each of which is located at a different location in the irrigation system. The test cells are individually connectable to the measuring instrument which is located at a control location; by way of a switching arrangement (not shown), enabling the impedance of each test cell to be measured.

Referring to FIG. 2 a moisture test cell, represented by block 32, is shown with its terminals G1 and G2 connected to the input terminals 12a and 12b by way of a suitable transmission line 31 which may be several hundred feet in length.

The circuits of the measuring instrument basically comprise a microcomputer 40 including a microprocessor, and associated input/output circuits 41, a program memory 42 and a data memory 44. The program memory 42 stores operating instructions for the microcomputer as well as table look-up data which is used in converting measured data to engineering units. The data memory 44 stores measured data. When the measure push-button 14 is operated to initiate a measurement cycle, the microprocessor is enabled and causes an excitation signal generator 46, embodied as a digital/analog converter, to generate a square wave excitation signal which is applied to the load connected to input terminals 12, including the soil test cell 32 and the transmission line 31. A monitoring circuit 52, embodied as an analog/digital converter, monitors the voltage across the load and provides to the microcomputer, a digital signal corresponding to the value of the load voltage. The microcomputer uses this signal to determine the amplitude and wave shape of the load voltage, and controls a line compensation network 48, which is interposed between the output of the digital/analog converter 46 and the load, to compensate as necessary for the effects of the transmission line 31.

The compensation network 48 includes a series range resistance section 49 and a shunt compensating capacitance section 50. The microcomputer, under program control, automatically selects the values of series resistance and shunt capacitance as a function of the load voltage measured.

The instrument has five ranges which are selected by auto-incrementing under microprocessor control. The ranges are defined as follows:

| Range | Load Resistance |
|---|---|
| 1 | 10 ohms to 5K ohms |
| 2 | 5K ohms to 50K ohms |
| 3 | 50K ohms to 500K ohms |
| 4 | 500K ohms to 2M ohms |
| 5 | 2M ohms to 10M ohms |

The series compensating resistance is selected to maintain the peak load voltage within 50% to 90% of the value of the signal generated by the digital/analog converter 46. In each measuring operation, range 1 is selected first, and if the load voltage is not within 50% to 90% of the value of the excitation signal, the next range is selected, and then the next range until the load voltage is within 50% to 90% of the excitation signal. Shunt compensating capacitance is added under microprocessor control whenever ranges 3, 4 or 5 are selected. The composition of the compensation network 48, as well as the auto-ranging and auto-compensation functions, are described in detail hereinafter.

When the auto-ranging and the auto-compensation functions have been completed, the microcomputer, via the analog/digital converter 52, samples the load voltage and averages the samples to provide an output corresponding to the impedance of the load, i.e. the transmission line and the test cell. The impedance of the moisture cell alone can be determined on the basis of previous knowledge of the transmission line impedance.

The microprocessor controls the digital display 16 via associated display drivers 54 to provide a four digit numerical display of the measured impedance.

In one measuring instrument which was constructed, the microprocessor 41 comprised the Type C8085A 8-bit microcomputer and suitable input/output circuits. The program memory 42 comprised a 2K×8-bit Type 2716 programmable read only memory, serving as instruction store, and a 1K×8-bit Type 2758 programmable read only memory, providing storage for table look-up data. The data storage memory 44 comprised two 256×4-bit Type 8561 CMOS random access memories. The digital display comprised a Type 7547 four-digit liquid crystal display unit which provides three digit resolution (except under 100 ohms) and one multiplier digit for readout of AC resistance. The display driver circuits 54 comprised four Type 4056BE LCD drivers. A comparator circuit 36, used for battery test operations, comprised a Type 311 H operational amplifier connected for operation as a differential amplifier. The compensating network 48, the digital/analog converter 46 and the analog/digital converter are shown in more detail in FIG. 3 and discussed hereinbelow.

The circuits of the measuring instrument are energized by a 12 volt rechargable battery source 33 which via DC/DC converter circuits 55 provide voltages at levels of ±15 VDC and +5 VDC for the circuits. A power switch 22, which is mounted on the control panel (FIG. 1) is operable to connect the DC/DC converter 55 to the battery source 33. A fuse 31 (FIG. 1), which is connected between the positive terminal of the battery and the power switch 22, affords overload protection for the circuits of the instrument.

The power circuits include a battery charger 34, which is connectable to an AC source via charge switch 24 and a connector 25, mounted on the control panel. The battery charger 34 enables the battery pack to be recharged when the instrument is not in use. An indicator 26 (FIG. 1) illuminates while the power pack is being charged.

Each time a measurement is requested, the comparator circuit 36 compares the battery voltage with a reference voltage and provides a signal at its output 36a indicative of the battery voltage. If the battery voltage is too low, the microprocessor causes the letters LLL to be displayed. Similarly, if the battery voltage is too high, the letters HHH are displayed. In either case, the measurement cycle is denied. The battery voltage may be checked at any time by operating the battery pushbutton 18 (FIG. 1), located on the panel 11, (FIG. 1) prior to and concurrently with the measure push-button 14 (FIG. 1).

After each measurement operation, the microprocessor circuits are deenergized, and the program memory 42 is switched to a standby mode, i.e. powered down, in order to conserve power. The circuits are reactivated during an initialization operation which occurs each time the measure push-button 14 is operated.

Compensation Network

Figure 3:
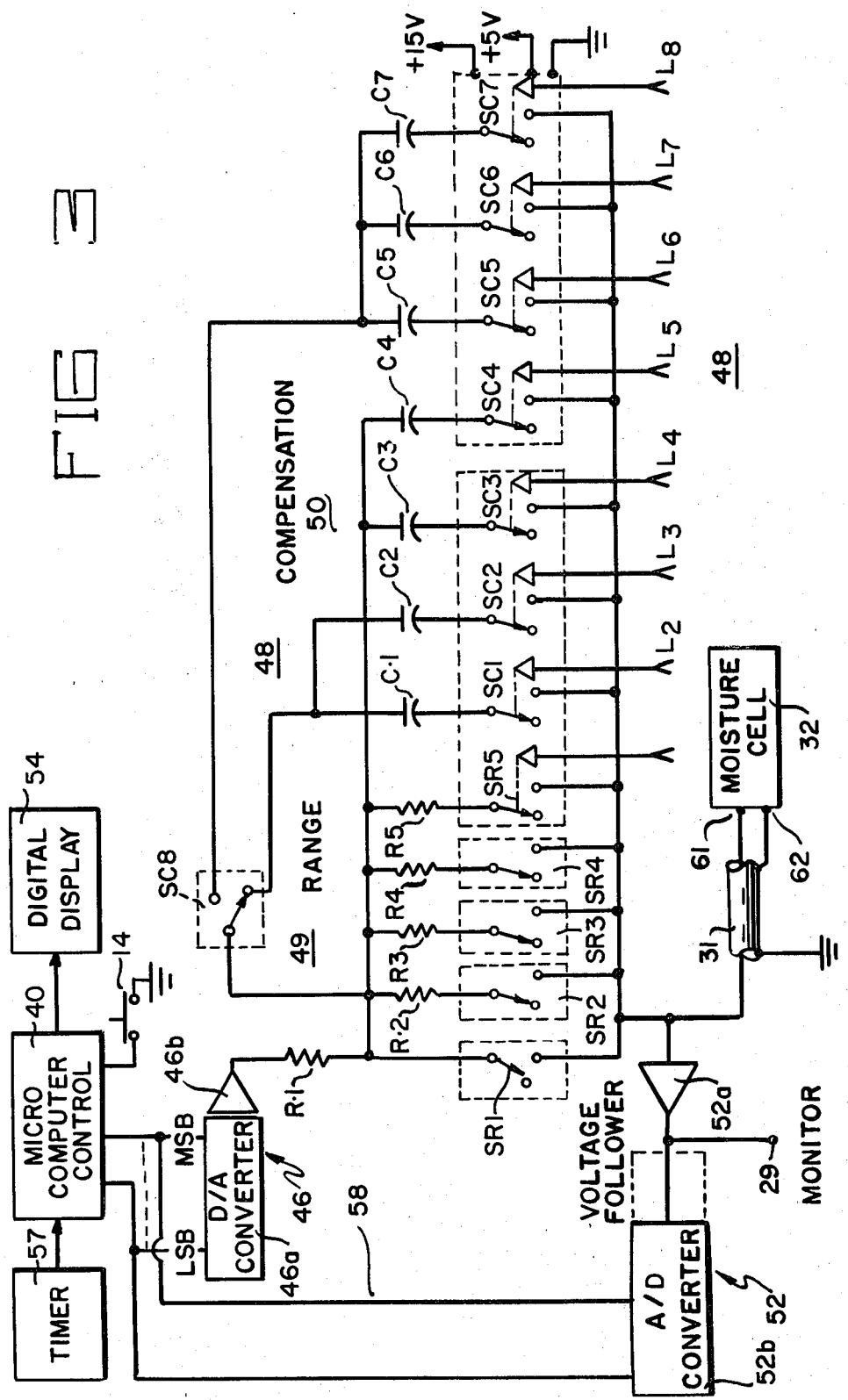
FIG. 3 is a partial schematic circuit and block diagram of the circuits of the measuring instrument.

Referring to FIG. 3, which illustrates the compensation network 48 in detail, the microprocessor, the memories and associated input/output circuits are represented by a block 40 which is labelled microcomputer control. The microcomputer communicates with the D/A converter circuit 46 and the A/D converter circuit 52 by way of a data bus 58. The measure switch 14 is connected to an input of the microprocessor over an associated anti-bounce circuit (not shown). A timer circuit 57, which operates asynchronously of the microprocessor clock, generates timing signals which serve as interrupts to the microprocessor to establish excitation frequency and data sampling rates. The function of this timer circuit 57 is described in more detail hereinbelow in connection with the discussion of the manner in which the output waveform is analyzed during the auto-compensation operation.

The digital/analog converter 46 comprises a commercially available type AD561K digital/analog converter circuit 46a and an associated output driver circuit 46b which is a Type 301AN operational amplifier. The microcomputer control provides a multi-bit control word to the digital/analog converter circuit 46a over a data bus 58. However, since only two of the bits are required to enable the digital/analog converter to provide a symmetrical square wave signal at a 15 VDC peak level, only the least significant bit LSB and the most significant bit MSB are extended to the signal inputs of the digital/analog converter, the unused signal inputs being commonly connected to the LSB input, for example.

The range network 49 comprises five resistors R1–R5 which are connectable in series with the output of the D/A converter 46 by way of associated switches SR1–SR5 which are operated under the control of the microcomputer. The switches SR1–SR4 are reed relays which present a substantially open impedance to the output of the D/A converter 46 when all of the switches are unoperated. Each reed switch has an associated driver (not shown) which receives an enabling signal from the microcomputer by way of associated I/O latches (not shown). Switch SR5 may be a solid state switch bus as one section of the commercially available Type AD-1510 DI quad MOS analog switch. A solid state switch may be used because resistor R5, its value of 4 megohms together with the off-resistance of the analog switch, normally presents a virtually open circuit. In one circuit, resistors R1–R5 had values of 1K, 9K, 99K, 1M, and 4M ohms, respectively.

The microcomputer generates outputs which are stored in its output latch circuits and are applied to inputs of the reed switch drivers for operating reed switches SR1–SR4, or to analog switch SR5, to select the desired range at the start of each measurement cycle. Range 1 is always selected first, and switch SR1 is operated to connect resistor R1 in series with the load. If the output voltage is not within a range of 50–90% of the square wave signal generated by the D/A converter 46, then switch SR2 is operated, connecting resistor R2 in series with resistor R1 and the load, thereby selecting range 2. Resistor R1 is connected in circuit for all five ranges to isolate the capacitors C1–C7 from the D/A converter output to assure that a non-capacitive load is presented to the D/A converter 46. To select range 3, switch SR2 is disabled, and switch SR3 is enabled. Similarly, switch SR4 (or SR5) is operated to select range 4 (or 5). The range resistance network together with the load operate as a voltage divider with the series range resistance being increased to "match" higher values of load impedance thereby lowering the voltage at the mounting point i.e. the junction of the series range resistance and the load.

The compensation network 50 comprises seven binary weighted capacitors C1–C7 each having an associated switching device SC1–SC7 represented by switch contacts. Each of the switches is operated under microcomputer control by computer generated outputs, provided over inputs L2–L8, to connect selected ones of the capacitors in parallel with the range resistance selected. Solid state switch devices, such as the commercially available type AD 7510 DI Quad MOS analog switches, are used to minimize power requirements and afford faster switching speeds than provided by the reed switches used in the range network. The slower speed reed switches can be used for range selection because during range selection the range is changed infrequently, i.e. typically two or three times. In one circuit which was constructed, capacitors C1–C7 had values of 500 pfd, 0.001 ufd, 0.002 ufd, 0.004 ufd, 0.008 ufd, 0.016 ufd and 0.032 ufd. respectively.

A switch SC8, which may be a reed switch operated under computer control, normally connects one terminal of capacitors C1 and C2 to the output circuit, thereby enabling capacitors C1 and C2 to be connected in circuit with the range resistance whenever switches SC1 and SC2 are operated. The switch SC8 is operable to connect one terminal of capacitors C5–C7 to the output circuit, and disconnect the capacitors C1 and C2 from the output circuit, thereby enabling capacitors C5–C7 to be connected in circuit with the range resistance. This switching arrangement minimizes the number of capacitors which are connected in the output circuit of the D/A converter circuit to reduce the effect of parallel leakage currents within circuit 50.

Auto-range/Auto-compensation

Figure 4:
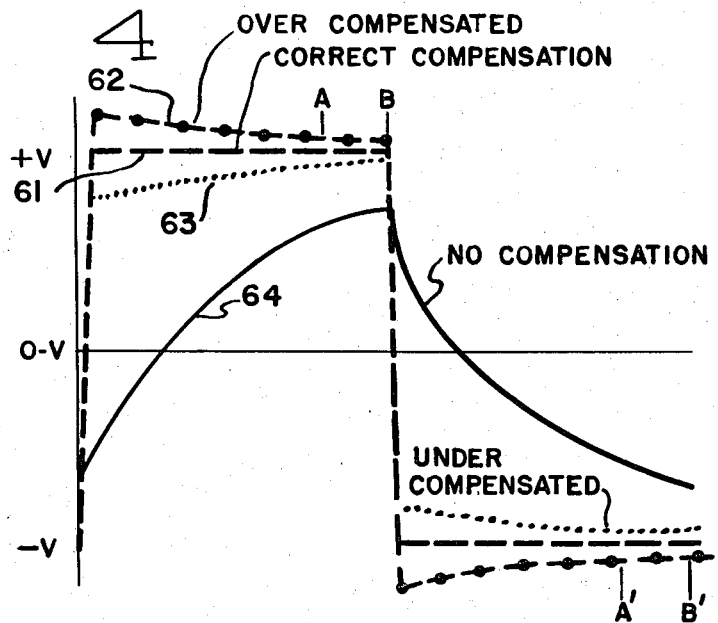
FIG. 4 illustrates typical output voltage levels for various levels of compensation.

The manner in which the microcomputer controls the selection of capacitors during an auto-compensation operation is described with reference to FIG. 4. At impedances over 100K ohms over several hundred feet of transmission line, the uncompensated output signal would look similar to curve 64 shown in FIG. 4. The addition of binary weighted capacitors C1–C7 in series with resistor R1, which together are in parallel with selected ones of the range resistors R2–R5 pre-charge the transmission line at a rate to provide correct compensation.

Generally, the compensated output voltage will approximate the form of the square wave excitation signal, represented by dashed line 61. Over-compensation results in a final voltage, waveform 62, which is too high, whereas under-compensation results in reaching a final voltage waveform 63, which is too low.

The microprocessor determines when the best compensation has been achieved by looking at point A-B, of the positive half cycle of the square wave output, and points A'-B' of the negative half cycle, and adding an increasing amount of compensating capacitance during each measurement cycle. When the voltage levels at points A and B (and A' and B') are equal, i.e. zero slope, then correct compensation has been achieved. It is pointed out that in some instances, zero slope may not be realized in which case a slightly negative slope is indicative of adequate compensation.

Output Voltage Sampling

Referring again to FIG. 3, the monitoring circuit 52 monitors the output voltage and provides to the microprocessor, via data bus 58, a ten bit digital signal representing the output voltage waveform. The monitoring circuit 52 comprises a high impedance buffer amplifier 52a, such as the Type LM 302H, operating as a voltage follower, and a high speed (25u sec.) A/D converter 52b, such as the commercially available Type AD 571K converter circuit, which digitizes and stores the measured data. The eight lower order bits are supplied to the microprocessor by way of a first I/O latch (not shown) and the two most significant bits are supplied to the microprocessor via a further I/O latch. The junction of buffer amplifier output and the A/D converter input is extended as a monitor point to a BNC connector 29 mounted on the control panel 11 (FIG. 1).

The timer circuit 57 comprises a clock tick oscillator, which operates asynchronously with respect to the microprocessor clock to generate interrupt signals for the microprocessor at a 1.6 KHZ rate. These interrupt signals provide reference for timing in generating the period of the square wave excitation signal and establish data sampling rates which enable the microprocessor to sample the load voltage near the leading and trailing edges of the positive and negative half cycles of the square wave signal.

The output voltage is sampled synchronously with the time circuit 57 and samples are accrued at a rate of eight samples per half cycle during a measurement cycle. For ranges one and two, the frequency of the excitation signal is 100 Hz, and for ranges three through five, a 50 Hz excitation signal is used. Samples are taken at the leading and trailing edges of each half cycle under microprocessor control.

The output voltage samples are used to determine the total impedance, including the impedance of the line and the moisture cell under test, by the equation:

$$Zm = \frac{Eo\, Rs}{Ea - Eo} \quad (1)$$

where:
Eo is the final output voltage (points B, B')
Rs is the series range resistance
Ea is the peak output voltage applied, and
Zm is the measured impedance This relationship is implemented using a look-up table stored in the read only memory 42.

The impedance of the moisture cell alone can only be determined by previous knowledge of the transmission line impedance. This is calculated at time of installation of the system. The equation for moisture cell impedance becomes $$Z1 = \frac{Zm\, Z2}{Z2 - Zm} \quad (2)$$

where:
Z1 is the moisture cell impedance
Z2 is the transmission line impedance
Zm is the measured impedance (Z1 Z2)

The effects of moisture cell polarization and hardware offset voltages are minimized by sampling both the positive and negative slopes of the output waveform.

Subprogram Hierachy

Figure 5:
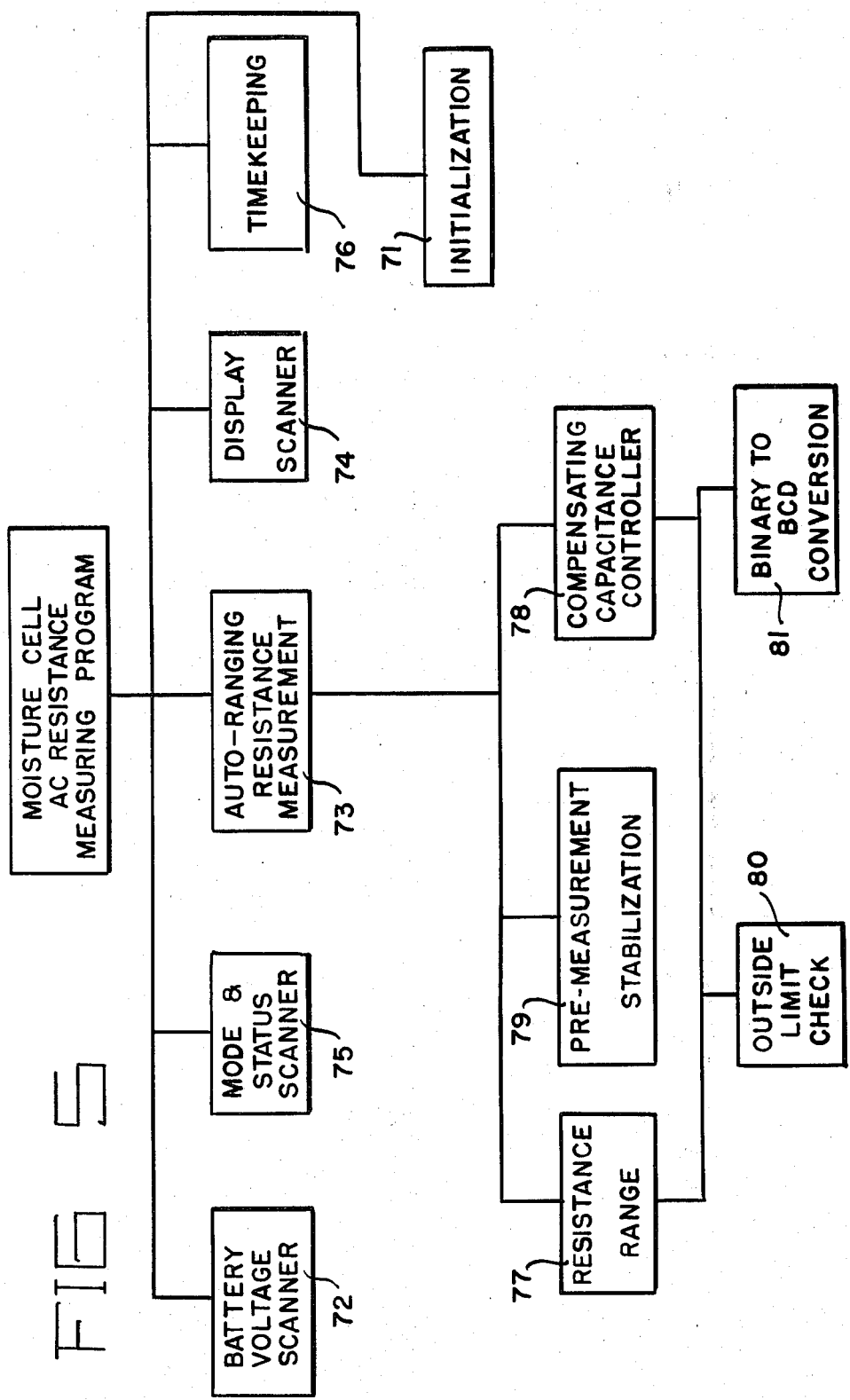
FIG. 5 is a control firmware hierachy block diagram.

Referring to FIG. 5, the control firmware subprogram hierachy is illustrated to provide an overview of the system program, a program listing for which is provided in appendix I. The subroutines include initialization (BEGIN) 71 starting at line 68; battery voltage scanner (BUSCAN) 72 beginning at line 984; auto-ranging resistance measurement (MEASUR) 73 beginning at line 156; and display scanner (DISPLY) 74 beginning at line 890. A mode and status scanner (STSCAN) 75, beginning at line 848, scans the status of panel mounted switches as well as the battery test flag, and a time keeping subroutine (IENTR) 76 generates the interrupt signals, at a rate of 0.625 milliseconds, for the microprocessor.

The auto-ranging resistance measurement subroutine includes resistance range routine (MAGAIN) 77, starting at line 194, which controls the incrementing of the resistance range, and a compensating capacitance controller (CAPINR) 78, beginning at line 719, which controls the connection of the compensating capacitance into the circuit. A stabilization routine (STABLS) 79, beginning at line 494, provides the delays during the measurement cycle to permit stabilization of the measured voltage before data is used. An outside limit check routine 80, starting at line 1024, determines when the measured voltage is out of range, and a binary to BCD conversion routine (BNBCT) 81, beginning at line 1046, controls the conversion of the binary data output of the A/B converter to decimal. The voltage/resistance lookup table is provided beginning at line 1096, and the ADC voltage to battery voltage table begins at line 1191.

Program Flow Chart

Figure 6:
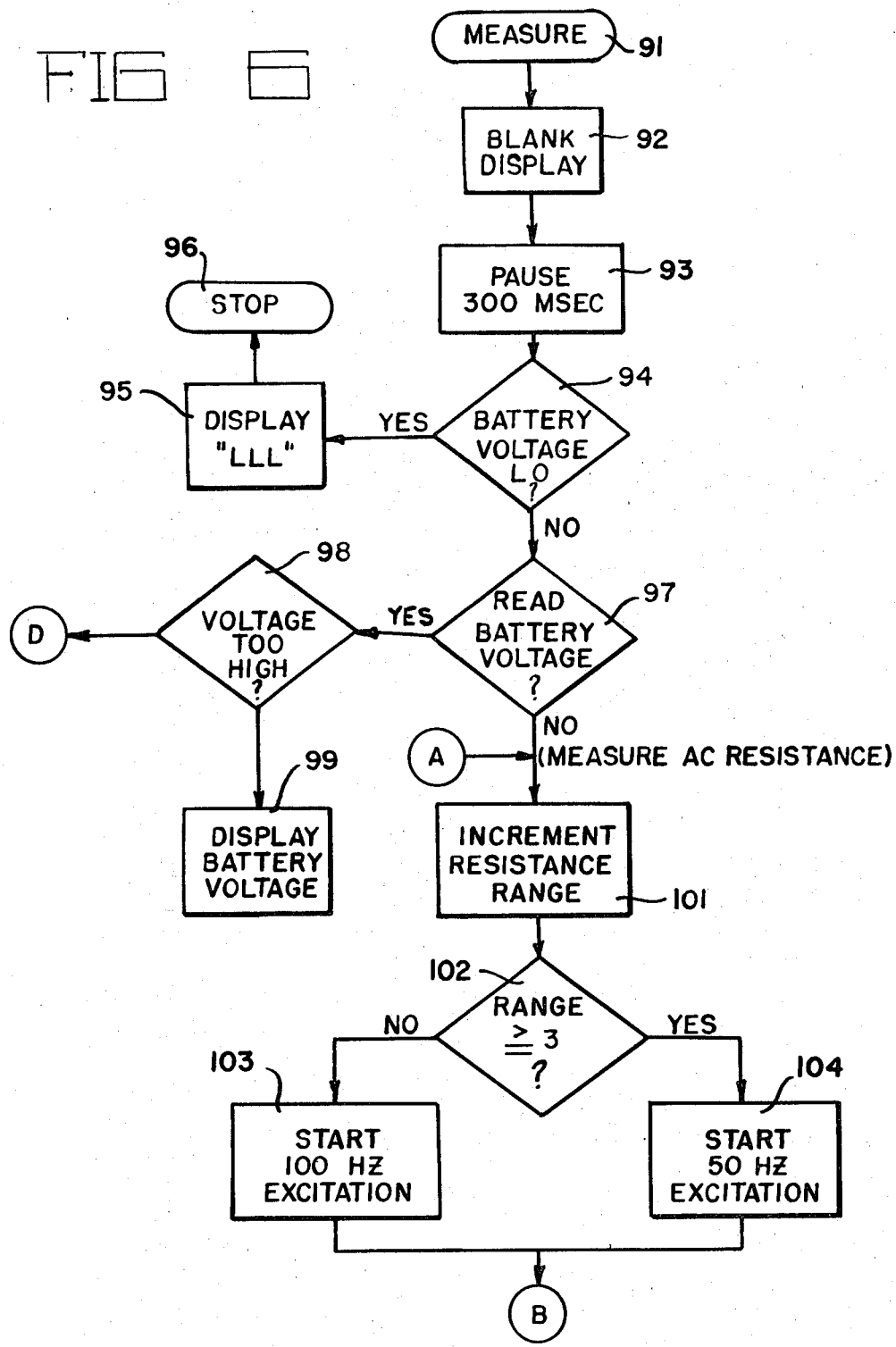
FIGS. 6-8 are a flow chart illustrating the operation of the instrument.
Figure 7:
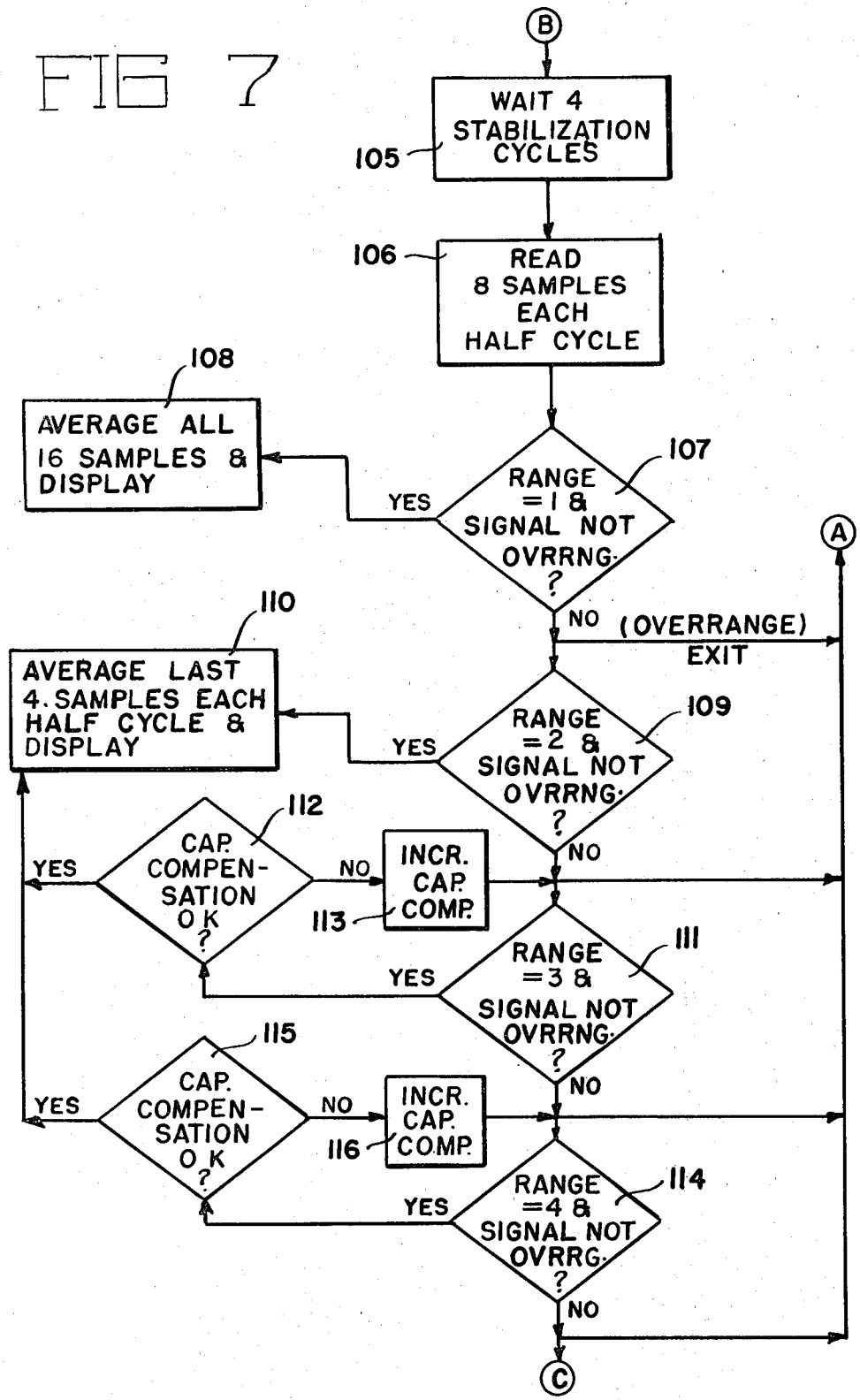
Figure 8:
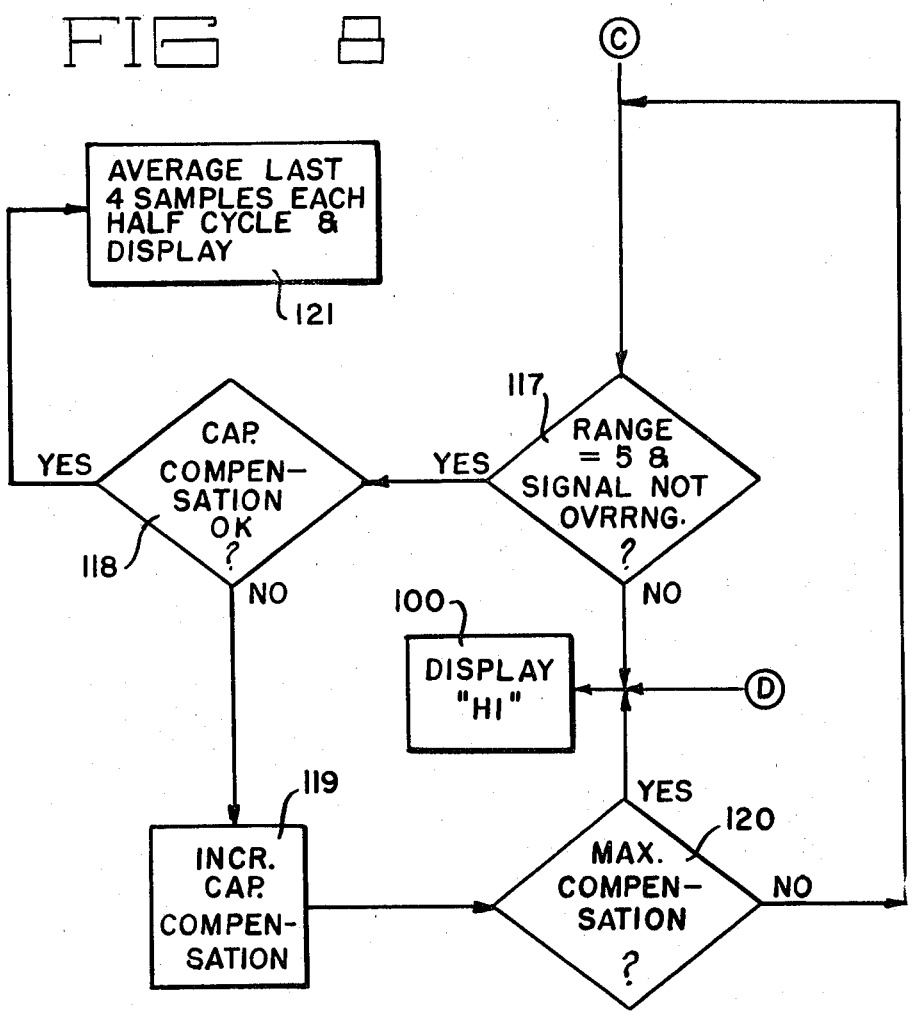

FIGS. 6 7, and 8 illustrate a flow chart for the program. The program consists of four basic operations namely: initialization; battery voltage check; autoranging measurement, including range selection, line compensation, and resistance calculation, and display.

Referring first to FIG. 6, the program functions are initiated in block 91 in response to the operation of the measure push-button 14 (FIG. 1). The initialization includes activating the circuits which are normally powered down between measurements. The program at block 92 causes the display to be blanked, and then at block 93, the program pauses for 300 milliseconds, allowing the circuits to stabilize after application of power.

At decision block 94, the status of the battery voltage comparator circuit 36 (FIG. 2) is read, and if the battery voltage is too low, the program advances to block 95 to cause the letters LLL to be displayed on display 16 (FIG. 1) and at block 96, halts the program, terminating the measurement cycle. If the battery voltage is above the minimum level, then at block 97-99, the status of the battery voltage push-button 18 (FIG. 1) is read to determine if this is a measurement cycle of a battery check operation. If the switch 18 is operated, then the battery voltage is read and displayed at block 99. If the battery voltage is too high, the program advances to block 100 (FIG. 8), and causes the letters HI to be displayed. This operation is provided both for battery test and during resistance measurement cycles.

Assuming that battery test switch 18 has not been operated, then after the battery voltage check operation, the program proceeds to the auto-ranging measurement operations. The first aspect of the auto-ranging operation is the selection of the range, and at block 101, range 1 is selected automatically at the beginning of each measurement operation. This causes resistor R1 to be connected in series with the load for the first measurement cycle, and for subsequent cycles, resistors R2, R3, etc. are connected in series with load until the correct resistance is found. At decision block 102, it is determined whether ranges 3, 4 or 5 have been selected and at blocks 103 and 104, the appropriate excitation signal frequency is selected as a function of the range presently selected. A 100 Hz signal is used for ranges 1 and 2, and a 50 Hz frequency signal is used for ranges 3-5.

Referring to FIG. 7, for all ranges, the program waits for four stabilization cycles at block 105 and then advances to block 106 to read eight samples during each half cycle, (a total of sixteen samples) during the final ninth cycle.

The program advances to block 107 where a test is made to determine if range 1 is selected. Also, the sixteen samples are averaged and the last value read is compared with the upper limit 5K ohms for range 1 to determine whether or not the signal is over range. Assuming that range 1 is selected and that the signal is not over range, then a block 108, the sixteen samples are averaged and displayed. If the upper limit for range 1 is exceeded, that the program returns to block 101 (FIG. 6) and the resistance range is incremented by one. The microcomputer causes switch SW2 (FIG. 3) to be operated, connecting resistor R2 in series with the load and resistor R1.

The program proceeds through blocks 102-107 as before, and since range 2 is now selected, the program advances to block 109. Assuming that the last value read is less than 50K ohms, the upper limit for range 2, then the program advances to block 110 where the last four readings of each half cycle are used for averaging and display. If, on the other hand, the last value read is greater than 50K ohms, then at block 109 the program returns to block 101 and selects range 3 by disabling switch SW2 and enabling switch SW3 to connect resistor R3 in series with the load in place of resistor R2.

When range 3 (or ranges 4 or 5) is selected, then at block 102, the program proceeds to block 104 to cause the frequency of the excitation signal to be changed from 100 Hz to 50 Hz. The program proceeds through blocks 105-109 and at block 111 the program determines that range 3 has been presently selected and uses the data read to determine whether or not the reading exceeds 500K ohms, the upper limit for range 3. Assuming that the value read is less than the upper limit for range 3, than at blocks 111-113, the program provides the auto-compensation function, adding an increasing amount of line compensation capacitance across the series limiting range resistor R3 until the positive waveform slope is compensated to a point where it becomes zero or a slightly negative slope. As described above with reference to FIG. 4, the slope of the excitation signal waveform is determined by looking at samples of the output voltage waveform near its leading and trailing edges in both positive and negative half cycles. The slope of the waveform is determined by averaging the absolute value of all sixteen samples. The average must be greater than or equal to the average of the last set of samples. If at any point along the way to compensating for line capacitance, the final reading exceeds 500K ohms, then the program returns to block 101 to select the next higher range. During the outer compensation operation, the microcomputer operates switches SC1-SC7 to initially increase line compensating capacitance in increments of 500 pf. If proper compensation is not achieved by the time capacitors C1-C4 are all connected in parallel across the range resistance, then switch SC8 is operated, disconnected capacitors C1 and C2 from the circuit, and enabling capacitors C5-C7 to be connected in parallel with the range resistance when their associated switches SC5-SC7 are operated under microcomputer control.

At block 112, the program determines when proper compensation has been achieved and then advances to block 110 where the last four samples for each half cycle, (eight samples) are averaged and displayed. If at block 111 the program determines that the final reading exceeds 500K ohms, then program returns to block 101 and selects range 4, causing resistor R4 to be connected in series with the load.

When range 4 is selected, the program operates in a manner identical to that when range 3 is selected, providing auto-compensation by way of blocks 114-116. If the final reading in any measurement cycle exceeds 2M ohms, the fifth range is selected at block 101.

Referring now to FIG. 8, the program operates for range five in a manner identical to that for ranges 3 and 4, with blocks 117-119 providing auto-compensation except that if the final reading in any measurement cycle is equal to or greater than 10M ohms, then block 120 terminates the measurement cycle and block 100 causes the message "HI" to be displayed to inform the user that either the AC resistance is to high or line capacitance is to great, or both. When proper compensation is achieved, then at block 121, the program averages the last four samples each half cycle and displays the averaged data.

APPENDIX - PROGRAM LISTING

TABLE OF CONTENTS FOR PROGRAM ACRM

| | LINE | PAGE |
|---|---|---|
| AC RESISTANCE MEASUREMENT | 17 | 1 |
| MAIN PROGRAM | 101 | 3 |
| MEASURE RESISTANCE | 156 | 4 |
| A/D CONVERT AND READ ROUTINE | 469 | 10 |
| STABILIZATION ROUTINES | 494 | 11 |
| TWOS COMPLEMENT | 597 | 13 |
| AVERAGE SAMPLES | 613 | 14 |
| CAPACITANCE COMPENSATION ROUTI | 719 | 16 |
| CORRECT COMPENSATION CHECK | 763 | 17 |
| CALIBRATE MODE PAUSE ROUTINE | 801 | 18 |
| VOLTAGE/RESISTANCE CONVERSION | 817 | 18 |
| STATUS SWITCH SCAN | 848 | 18 |
| BATTERY LOW MESSAGE | 869 | 19 |
| DISPLAY DRIVER | 890 | 20 |
| BATTERY VOLTAGE READ/DISPLAY | 984 | 22 |
| OUT OF RANGE 'HI' MESSAGE | 1024 | 22 |
| 16 BIT BINARY TO BCD CONVERSIO | 1046 | 24 |
| LOOK-UP TABLES | 1096 | 25 |
| VARIABLES | 1217 | 30 |
| CONSTANTS | 1243 | 31 |

```
ERR LINE        STATEMENT

1      LSTOFF
 17      TITLE AC RESISTANCE MEASUREMENT
 18      ;----------------------------------------------------
 19      ;
 20      ; MOISTURE CELL RESISTANCE MEASUREMENT
 21      ;     WITH LINE CAPACITANCE COMPENSATION
 22      ;
 23      ;    FEATURING - AN 8085 MICROPROCESSOR CONTROLLED ALGORITHM
 24      ;         WITH THE FOLLOWING CAPABILITIES:
 25      ;
 26      ;    AUTO-RANGING: 1=0-5K, 2=5K-50K, 3=50K-500K
 27      ;                  4=500K-2M, 5=2M-999M OHM
 28      ;
 29      ;    AUTO-PARALLEL LINE CAPACITANCE COMPENSTATION
 30      ;         TO 0025UF (EXCEPT LOWER TWO RANGES)
 31      ;
```

```
32   ;        BY PJ HOF
33   ;        BATTELLE-NORTHWEST
34   ;        AUGUST 1979
35   ;        R1: NOV. 1979
36   ;
37   ;------------------------------------------------------------
38   ;
39   ;        DEFAULT BASE IS 10
40   ;        M85EXT.ASM INCLUDED FOR EXTENDED INSTRUCTION SET
41   ;
42   ;------------------------------------------------------------
43   ; POWER UP - MEASURE INITIALIZATION
44   ;------------------------------------------------------------
45           ORG     0
46           LXI     SP,10077Q    ; 62 BYTES RESERVED FOR STACK
47           JMP     BEGIN
48   ;
49   ;------------------------------------------------------------
50   ;
51   ; TIMER INTERRUPT (RST 7.5)
52   ;        (PERIOD APPROX 0.625 MILLISECONDS)
53   ;
54   ;------------------------------------------------------------
55           ORG     74Q
56           PUSH    PSW
57           PUSH    H
58           LHLD    RATCON
59           INX     H
60           SHLD    RATCON
61           POP     H
62           POP     PSW
63           EI
64           RET
65   ;
66   ;------------------------------------------------------------
67   ;
68   BEGIN:
69   ; CLEAR ALL PROGRAM VARIABLES
70           LXI     H,RAMSTART
```

ERR LINE              STATEMENT

```
71             LXI     D,RAMSTART-RAMEND
72             LXI     B,1
73   LT1:      MVI     M,0
74             INX     H
75             XCHG
76             DAD     B
77             XCHG
78             JNC     LT1
79   ; ENABLE INTERRUPTS AND MEASUREMENT
80   ;        CLEAR RUN LED, TOO
81             MVI     A,113Q
82             SIM
83             EI
84   ; REMOVE EXCITATION FROM CELL BEING MEASURED, IF ANY
85             MVI     A,DAZERO
86             STA     RNGSAV
87             OUT     RNPORT
88   ; BLANK DISPLAY
89             MVI     A,17Q
```

```
 90              OUT     DISPM
 91              OUT     DISP3
 92              OUT     DISP2
 93              OUT     DISPL
 94      ; PAUSE APROXIMATELY 300MSEC
 95              LXI     H,RATCON+1
 96      LT100:  MOV     A,M         ; GET 512 BIT IN CARRY
 97              RAR
 98              RAR
 99              JNC     LT100
100
```

ERR LINE            STATEMENT

```
101     SBTTL MAIN PROGRAM
102     ;===========================================
103     ;
104     ; MAIN PROGRAM CONTROLLING LOOP
105     ;
106     ;===========================================
107     LOOP:
108     ; SCAN STATUS AND SWITCHES
109             CALL    STSCAN
110             PUSH PSW        ; SAVE CARRY FLAG
111     ;-IF (BATTERY VOLTAGE LOW)
112             LDA     CNFLAG
113             RAL
114             JNC     @A10
115     ;-THEN OUTPUT 'LLL' ON DISPLAY
116             CALL    VLDISP
117             JMP     @A50
118     ;-ELSE
119     ;--IF (CARRY SET FROM STSCAN) THEN READ BATTERY VOLTAGE
120     @A10:   POP     PSW
121             JNC     @A20
122             CALL    BVSCAN  ; BATTERY VOLTAGE INTO D,E
123     ;       SET RANGE=1, EXCITATION=0
124             MVI     A,201Q
125             STA     RNGSAV
126             LXI     H,BCDBUF    ; BUFFER POINTER INTO H,L
127             JMP     @A50    ; CARRY SET, OUTPUT 'HI'
128     ;--ELSE MEASURE AC RESISTANCE
129     @A20:   CALL    MEASUR
130     ;--ENDIF
131     ;-ENDIF
132     ; DISPLAY MEASUREMENT/MESSAGE
133     @A50:   CALL DISPLY
134     ;-IF (CALIBRATE MODE)
135             LDA     CNFLAG
136             RAL
137             RAL
138             JNC     @A100
139     ;-THEN PAUSE 2 SECONDS
140             CALL    CWAIT
141             RST     0           ; REPEAT 'MEASUREMENT CYCLE'
142     ;-ELSE GO TO SLEEP
143     ;       RETURN RANGE AND EXCITATION TO ZERO
```

```
144   •A10•:  MVI    A,DAZERO
145           OUT    RNPORT
146           XRA    A
147           OUT    CNPORT
148           MVI    A,166Q  ; HALT INSTRUCTION
149           STA    SLEEP   ; CMOS RAM ADDRESS
150   ;      MASK ALL INTERRUPTS AND RUN LED
151           MVI    A,177Q
152           SIM
153           JMP    SLEEP   ; PROM MEMORY DESELECTED
154   ;-ENDIF
155
```

R LINE                STATEMENT

```
156   SBTTL MEASURE RESISTANCE
157   ;----------------------------------------------------------
158   ;
159   ; MEASURE AC RESISTANCE WITH AUTO LINE
160   ;         CAPACITANCE COMPENSATION
161   ;
162   ;     INPUTS:
163   ;       RATE CONTROL COUNTER (RATCON)
164   ;       RANGE,CONVERT,EXCITATION SAVE (RNGSAV)
165   ;
166   ;     OUTPUTS:
167   ;       RANGE SAVE (RNGSAV)
168   ;       BCD BUFFER POINTER (MSB) IN H,L
169   ;
170   ;----------------------------------------------------------
171   MEASUR:
172   ; INCREMENT RESISTANCE RANGE
173   ;-IF (CURRENT RANGE .EQ. 0) THEN SET RANGE .EQ. 1
174           LDA    RNGSAV
175           MOV    B,A
176           ANI    37Q      ; MASK RANGE
177           CPI    0
178           JNZ    A1•
179           MOV    A,B
180           ADI    1
181           STA    RNGSAV
182           OUT    PNPORT
183           JMP    MAGAIN
184   ;-ELSE SHIFT RANGE BIT LEFT 1
185   A1•:    RLC
186           MOV    C,A      ; SAVE NEW RANGE BIT
187           MOV    A,B
188           ANI    340Q     ; MASK NON-RANAGE BITS
189           ADD    C        ; ADD TO RANGE BIT
190           STA    RNGSAV
191           OUT    RNPORT
192   ;-ENDIF
193   ; WAIT FOR INTERVAL SYNC (64 COUNT BIT)
194   MAGAIN: LXI    H,RATCON        ; COUNTER POINTER (LSB)
195           MVI    A,276Q   ; XX64-2
196           MOV    M,A
197   A3•:    LDA    RATCON
198           RAL             ; BIT 6 INTO CARRY (6 OF 8)
```

```
199              RAL
200              JNC     A3@
201     ; DETERMINE RATE & START POSITIVE EXCITATION
202     ;-IF (RANGE .GE. 3)
203              LDA     RNGSAV
204              MOV     B,A
205              ANI     37Q         ; RANGE BITS
206              CPI     4           ; RANGE 3
207              JM      A4@
208              MOV     A,B
209     ;-THEN RATE IS 50HZ
210              ORI     DAPLUS      ; PLUS EXCITATION
```

ERR LINE                STATEMENT

```
211              STA     RNGSAV
212              OUT     RNPORT
213              MVI     A,2
214              STA     INCR12
215              JMP     A5@
216     ;-ELSE RATE IS 100HZ
217     A4@:     ORI     DAPLUS      ; PLUS EXCITATION
218              STA     RNGSAV
219              OUT     RNPORT
220              MVI     A,1
221              STA     INCR12
222     ;-ENDIF
223     ; WAIT FOUR CYCLES FOR STABILIZATION
224     A5@:     CPI     1
225              JZ      A6@
226              CALL    STABLS      ; 50HZ RATE
227              JMP     A10@
228     A6@:     CALL    STABLF      ; 100HZ RATE
229     ; READ AND STORE 16 SAMPLES, 8 FOR EACH HALF CYCLE
230     A10@:    MVI     C,20Q       ; SET NO OF SAMPLES COUNTER
231              LDA     INCR12      ; GET RATE TO SAMPLE
232              MOV     B,A
233              LXI     H,SAMPLE              ; SAMPLE BUFFER POINTER
234     A11@:    LDA     RATCON
235              ANI     77Q         ; MASK INTERVAL BITS
236              CMP     B
237              JNZ     A11@        ; WAIT UNTIL SAMPLE TIME
238              CALL    CONVRD      ; CONVERT AND READ SAMPLE
239     ;        MOV SAMPLE IN D,E TO MEMORY BUFFER
240              MOV     M,E
241              INX     H
242              MOV     M,D
243              INX     H
244     ;        SET UP NEXT SAMPLE INTERVAL COMPARE
245              LDA     INCR12
246              ADD     B
247              MOV     B,A
248              DCR     C
249              MOV     A,C
250              JZ      A12@
251              CPI     10Q         ; END HALF CYCLE
252              JNZ     A11@
```

```
253             LDA     RNGSAV    ; OUTPUT NEGATIVE EXCITATION
254             ANI     77Q
255             STA     RNGSAV
256             OUT     RNPORT
257             JMP     A110      ; CONTINUE FOR 16 SAMPLES
258     ; SAMPLES TAKEN, READ RUN BIT 1024
259     ;       LITE RUN LED WHILE HI (=1)
260     A120:   LDA     RATCON+1            ; MSB
261             ANI     2
262             JNZ     A130
263             MVI     A,100Q    ; TURN LED OFF
264             SIM
265             JMP     A140
```

LINE            STATEMENT

```
266     A130:   MVI     A,300Q    ; TURN LED ON
267             SIM
268     ; TURN OFF EXCITATION
269     A140:   LDA     RNGSAV
270             ANI     77Q
271             ORI     DAZERO
272             STA     RNGSAV
273             OUT     RNPORT
274     ;=IF (CURRENT RANGE .EQ. 1)
275             LDA     RNGSAV
276             ANI     37Q
277             CPI     1
278             JNZ     A200
279     ;--IF (LAST POSITIVE SAMPLE NOT OVERRANGE)
280             LHLD    SAMPLE+14           ; SAMPLE
281     ;---IF (NEGATIVE VOLTAGE) THEN SKIP TEST
282             MOV     A,H
283             ANI     2
284             JZ      A170
285     ;---ELSE STRIP SIGN BIT
286             MOV     A,H
287             ANI     1
288             MOV     H,A
289     ;---ENDIF
290             LXI     B,427     ; R X 5 LIMIT
291             DSUB
292
293             JNC     A150
294     ;--THEN AVERAGE ALL 16 SAMPLES
295     A170:   MVI     B,10Q     ; 8/HALF CYCLE SAMPLES
296             LXI     H,SAMPLE            ; BUFFER POINTER
297             CALL    AVE1
298             JMP     A160
299     ;--ELSE INCREMENT RANGE AND TRY AGAIN
300     A150:   JMP     MEASUR
301     ;--ENDIF
302     ;-THEN CONVERT VOLTAGE TO RESISTANCE
303     A160:   CALL    VRCONV
304     ; MEASUREMENT COMPLETE
305             RET
306     ;=ENDIF
```

```
307        ;-IF (CURRENT RANGE .EQ. 2)
308   A200: CPI     2
309         JNZ     A300
310        ;--IF (LAST POSITIVE SAMPLE NOT OVERRANGE)
311         LHLD    SAMPLE+14       ; SAMPLE
312        ;        STRIP SIGN BIT
313         MOV     A,H
314         ANI     1
315         MOV     H,A
316         LXI     B,427           ; R X 5 LIMIT
317         DSUB
318
319         JNC     A210
320        ;--THEN AVERAGE LAST 8 (4 PER HALF CYCLE)
```

ERR LINE              STATEMENT

```
321         MVI     B,4             ; 4/HALF CYCLE SAMPLES
322         LXI     H,SAMPLE        ; BUFFER POINTER
323         CALL    AVE1
324         JMP     A220
325        ;--ELSE INCREMENT RANGE AND TRY AGAIN
326   A210: JMP     MEASUR
327        ;--ENDIF
328        ;-THEN CONVERT VOLTAGE TO RESISTANCE
329   A220: CALL    VRCONV
330        ; MEASUREMENT COMPLETE
331         RET
332        ;-ENDIF
333        ;-IF (CURRENT RANGE .EQ. 3)
334   A300: CPI     4
335         JNZ     A400
336        ;--IF (LAST POSITIVE SAMPLE NOT OVERRANGE)
337         LHLD    SAMPLE+14       ; SAMPLE
338        ;        STRIP SIGN BIT
339         MOV     A,H
340         ANI     1
341         MOV     H,A
342         LXI     B,427           ; R X 5 LIMIT
343         DSUB
344
345         JNC     A310
346        ;--THEN AVERAGE LAST 8 (4 PER HALF CYCLE)
347         MVI     B,4             ; 4/HALF CYCLE SAMPLES
348         LXI     H,SAMPLE        ; BUFFER POINTER
349         CALL    AVE1
350         JMP     A320
351        ;--ELSE INCREMENT RANGE AND TRY AGAIN
352   A310: XRA     A
353         OUT     CNPORT          ; REMOVE COMPENSATION
354         STA     CAPSAV
355         JMP     MEASUR
356        ;--ENDIF
357        ;--IF (COMPENSATION CORRECT - LAST 50% LEVEL)
358   A320: CALL    COMPCK
359         JC      A330
```

```
360         ;--THEN CONVERT VOLTAGE TO RESISTANCE
361             CALL    VRCONV
362         ; MEASUREMENT COMPLETE
363             RET
364         ;--ELSE INCREASE COMPENSATION
365     A330:
366         ;---IF (NOT MAXIMUM COMPENSATION)
367         ;---THEN INCREMENT CAPACITANCE
368             CALL    CAPINR
369             JC      A340
370         ;           AND RETURN TO TRY AGAIN
371             JMP     MAGAIN
372         ;---ELSE OUTSIDE CAP RANGE, OUTPUT 'HI' MESSAGE
373     A340:   CALL    HI
374             RET
375         ;---ENDIF
```

| LINE | STATEMENT |
|---|---|

```
376         ;--ENDIF
377         ;-ENDIF
378         ;-IF (CURRENT RANGE .EQ. 4)
379     A409:   CPI     8
380             JNZ     A500
381         ;--IF (LAST POSITIVE SAMPLE NOT OVERRANGE)
382             LHLD    SAMPLE+14       ; SAMPLE
383         ;       STRIP SIGN BIT
384             MOV     A,H
385             ANI     1
386             MOV     H,A
387             LXI     B,342       ; R X 2 LIMIT
388             DSUB
389
390             JNC     A410
391         ;--THEN AVERAGE LAST 8 (4 PER HALF CYCLE)
392             MVI     B,4         ; 4/HALF CYCLE SAMPLES
393             LXI     H,SAMPLE    ; BUFFER POINTER
394             CALL    AVE1
395             JMP     A420
396         ;--ELSE INCREMENT RANGE AND TRY AGAIN
397     A410:   XRA     A           ; REMOVE COMPENSATION
398             STA     CAPSAV
399             OUT     CNPORT
400             JMP     MEASUR
401         ;--IF (COMPENSATION CORRECT - LAST 50% LEVEL)
402     A420:   CALL    COMPCK
403             JC      A430
404         ;--THEN CONVERT VOLTAGE TO RESISTANCE
405             CALL    VRCONV
406         ; MEASUREMENT COMPLETE
407             RET
408         ;--ELSE INCREASE COMPENSATION
409     A430:
410         ;---IF (NOT MAXIMUM COMPENSATION)
411         ;---THEN INCREMENT CAPACITANCE
412             CALL    CAPINR
```

```
413            JC      A440
414     ;      AND RETURN TO TRY AGAIN
415            JMP     MAGAIN
416     ;---ELSE OUTSIDE CAP RANGE, OUTPUT 'HI' MESSAGE
417     A440:  CALL    HI
418            RET
419     ;---ENDIF
420     ;--ENDIF
421     ;-ENDIF
422     ;-IF (CURRENT RANGE GT 4)
423     A50:
424     ;--IF (LAST POSITIVE SAMPLE NOT OVERRANGE)
425            LHLD    SAMPLE+14       ; SAMPLE
426     ;      STRIP SIGN BIT
427            MOV     A,H
428            ANI     1
429            MOV     H,A
430            LXI     B,366           ; R X 2.5 (10MEG OHM)
```

ERR LINE            STATEMENT

```
431            DSUB
432
433            JNC     A51
434     ;--THEN AVERAGE LAST 8 (4 PER HALF CYCLE)
435            MVI     B,4     ; 4/HALF CYCLE SAMPLES
436            LXI     H,SAMPLE        ; BUFFER POINTER
437            CALL    AVE1
438            JMP     A52
439     ;--ELSE OUTPUT 'HI' TO INDICATE OUTSIDE RANGE
440     A51:   CALL    HI
441            RET
442     ;--ENDIF
443     ;--IF (COMPENSATION CORRECT - LAST 50% LEVEL)
444     A52:   CALL    COMPCK
445            JC      A53
446     ;--THEN CONVERT VOLTAGE TO RESISTANCE
447            CALL    VRCONV
448     ; MEASUREMENT COMPLETE
449            RET
450     ;--ELSE INCREASE COMPENSATION
451     A53:
452     ;---IF (NOT MAXIMUM COMPENSATION)
453     ;---THEN INCREMENT CAPACITANCE
454            CALL    CAPINR
455            JC      A54
456     ;      AND RETURN TO TRY AGAIN
457            JMP     MAGAIN
458     ;---ELSE OUTSIDE RANGE, OUTPUT 'HI' MESSAGE
459     A54:   CALL    HI
460            RET
461     ;---ENDIF
462     ;--ENDIF
463     ;-ENDIF
464
```

| ERR | LINE | STATEMENT | | |
|---|---|---|---|---|
| | 465 | ;---------------------------------------------- | | |
| | 466 | ; UTILITY ROUTINES | | |
| | 467 | ;---------------------------------------------- | | |
| | 468 | ; | | |
| | 469 | SBTTL A/D CONVERT AND READ ROUTINE | | | |
| | 470 | ;---------------------------------------------- | | |
| | 471 | ; A/D CONVERT AND READ ROUTINE | | |
| | 472 | ;---------------------------------------------- | | |
| | 473 | CONVRD: | | | |
| | 474 | ; | OUTPUT CONVERT PULSE | | |
| | 475 | | LDA | RNGSAV | |
| | 476 | | ORI | ADCONV | |
| | 477 | | OUT | RNPORT | |
| | 478 | | NOP | | |
| | 479 | | LDA | RNGSAV | |
| | 480 | | OUT | RNPORT | |
| | 481 | | NOP | | |
| | 482 | B1: | RIM | | |
| | 483 | | RAL | | |
| | 484 | | JNC | B1 | ; WAIT FOR CONVERSION |
| | 485 | ; | READ CONVERSION | | |
| | 486 | | IN | ADCLB | |
| | 487 | | MOV | E,A | ; SAVE 10 BITS IN D,E |
| | 488 | | IN | ADSTAT | |
| | 489 | | ANI | 3 | |
| | 490 | | MOV | D,A | |
| | 491 | | RET | | |
| | 492 | ; | | | |
| | 493 | | | | |

| ERR | LINE | STATEMENT | | |
|---|---|---|---|---|
| | 494 | SBTTL STABILIZATION ROUTINES | | | |
| | 495 | ;---------------------------------------------- | | |
| | 496 | ; 100 HZ STABILIZATION | | |
| | 497 | ;---------------------------------------------- | | |
| | 498 | STABLF: | | | |
| | 499 | ; WAIT EIGHT CYCLES (100HZ) | | | |
| | 500 | ; | INCREMENT C EACH INCREMENT OF RATCON COUNTER | | |
| | 501 | | MVI | C,0 | ; RATE COUNTER |
| | 502 | | MOV | D,C | ; NO OF CYCLES |
| | 503 | C1: | LDA | RATCON | |
| | 504 | | RAR | | |
| | 505 | | JNC | C1 | ; WAIT FOR LO TO HI TRANSITION |
| | 506 | | INR | C | |
| | 507 | C2: | LDA | RATCON | |
| | 508 | | RAR | | |
| | 509 | | JC | C2 | ; WAIT FOR HI TO LO TRANSITION |
| | 510 | | INR | C | |
| | 511 | | MOV | A,C | |
| | 512 | | CPI | 10Q | ; 5MSEC HALF CYCLE |
| | 513 | | JNZ | C1 | |
| | 514 | | MVI | C,0 | ; RESET COUNTER |
| | 515 | ; | OUTPUT NEGATIVE EXCITATION FOR SAME INTERVAL | | |

```
516              LDA      RNGSAV
517              ANI      77Q        ; NON-EXCITATION DATA SAVE
518      ;                                AND NEGATIVE EXCITATION
519              STA      RNGSAV
520              OUT      RNPORT
521      C3@:    LDA      RATCON
522              RAR
523              JNC      C3@        ; WAIT FOR LO TO HI TRANSITION
524              INR      C
525      C4@:    LDA      RATCON
526              RAR
527              JC       C4@        ; WAIT FOR HI TO LO TRANSITION
528              INR      C
529              MOV      A,C
530              CPI      10Q        ; 5MSEC HALF CYCLE
531              JNZ      C3@
532      ; START POSITIVE EXCITATION
533              LDA      RNGSAV
534              ORI      DAPLUS
535              STA      RNGSAV
536              OUT      RNPORT
537      ;-IF (8TH CYCLE) THEN STABILIZATION COMPLETE
538              INR      D
539              MOV      A,D
540              CPI      8
541              RZ
542      ;-ELSE OUTPUT ANOTHER CYCLE
543              MVI      C,0        ; RESET RATE COUNTER
544              JMP      C1@
545      ;-ENDIF
546      ;
547      ;----------------------------------------------
548      ;        50 HZ STABILIZATION
549      ;----------------------------------------------
550      STABLS:
551      ; WAIT FOUR CYCLES (50HZ)
552      ;    INCREMENT C EACH HI TO LO OF RATCON LS BIT
553              MVI      C,0        ; RATE COUNTER
554              MOV      D,C        ; NO OF CYCLES
555      D1@:    LDA      RATCON
556              RAR
557              JNC      D1@        ; WAIT FOR HI TRANSITION FIRST
558      D2@:    LDA      RATCON
559              RAR
560              JC       D2@        ; WAIT FOR HI TO LO TRANSITION
561              INR      C
562              MOV      A,C
563              CPI      10Q        ; 10MSEC HALF CYCLE
564              JNZ      D1@
565      ; OUTPUT NEGATIVE EXCITATION FOR SAME PERIOD
566              LDA      RNGSAV
567              ANI      77Q        ; NON-EXCITATION DATA SAVE
568      ;                                AND NEGATIVE EXCITATION
569              STA      RNGSAV
570              OUT      RNPORT
571              MVI      C,0        ; RESET RATE COUNTER
```

```
572  D3@:    LDA     RATCON
573          RAR
574          JNC     D3@         ; WAIT FOR HI TRANSITION FIRST
575  D4@:    LDA     RATCON
576          RAR
577          JC      D4@         ; WAIT FOR HI TO LO TRANSITION
578          INR     C
579          MOV     A,C
580          CPI     10Q         ; 10MSEC HALF CYCLE
581          JNZ     D3@
582  ;       START POSITIVE EXCITATION
583          LDA     RNGSAV
584          ORI     DAPLUS
585          STA     RNGSAV
586          OUT     RNPORT
587  ;-IF (4TH CYCLE) THEN STABILIZATION COMPLETE
588          INR     D
589          MOV     A,D
590          CPI     4
591          RZ
592  ;-ELSE OUTPUT ANOTHER CYCLE
593          MVI     C,0         ; RESET RATE COUNTER
594          JMP     D1@
595  ;-ENDIF
596
597  SBTTL TWOS COMPLEMENT
598  ;-------------------------------------------------------
599  ;        PERFORM 2'S COMPLEMENT ON 9 BIT NEGATIVE NUMBER
600  ;-------------------------------------------------------
601  TWCOMP: MOV     A,D         ; NEGATIVE NUMBER IN D,E
602          ANI     1
603          RAR
604          CMC                 ; COMPLEMENT MS BIT
605          RAL
606          MOV     D,A
607          MOV     A,E
608          CMA                 ; COMPLEMENT 8 LS BITS
609          MOV     E,A
610          INX     D           ; ADD 1
611          RET
612
613  SBTTL AVERAGE SAMPLES
614  ;-------------------------------------------------------
615  ;
616  ; AVERAGE POSITIVE AND NEGATIVE SAMPLES (9 BITS)
617  ;
618  ;        INPUTS:
619  ;        NUMBER OF SAMPLES PER HALF CYCLE IN REG B
620  ;        SAMPLE BUFFER POINTER IN H,L
621  ;
622  ;        OUTPUT:
623  ;        AVERAGE OF VOLTAGE/RESISTANCE (PRCOVR)
624  ;
625  ;-------------------------------------------------------
626  AVE1:
627  ; SUM POSITIVE SAMPLES FIRST
```

```
628              MOV    C,B      ; SAVE NO OF POSITIVE SAMPLES
629              MVI    A,10Q    ; ADJUST BUFFER POINTER
630              SUB    B
631     E11*:    DCR    A
632              JM     E12*
633              INX    H
634              INX    H
635              JMP    E11*
636     E12*:    MOV    E,M      ; SAMPLES INTO D,E
637              INX    H
638              MOV    D,M
639              INX    H
640     ;-IF (NEGATIVE NUMBER) THEN 2'S COMPLEMENT
641              MOV    A,D
642              ANI    2
643              CZ     TWCOMP
644     ;-ELSE STRIP SIGN BIT ONLY
645              MOV    A,D
646              ANI    1
647              MOV    D,A
648     ;-ENDIF
649              PUSH   D        ; FIRST SAMPLE SAVED IN TOS
650              DCR    B
651              JZ     E5*
652     E1*:     MOV    E,M
653              INX    H
654              MOV    D,M
655              INX    H
656     ;-IF (NEGATIVE NUMBER) THEN 2'S COMPLEMENT
657              MOV    A,D
658              ANI    2
659              CZ     TWCOMP
660     ;-ELSE STRIP SIGN BIT ONLY
661              MOV    A,D
662              ANI    1
663              MOV    D,A
664     ;-ENDIF
665              XTHL            ; PREVIOUS SUM INTO H,L
666              DAD    D        ; ADD CURRENT SAMPLE TO SUM
667              XTHL            ; ADDRESS POINTER INTO H,L
```

ERR LINE              STATEMENT

```
668              DCR    B
669              JNZ    E1*
670     ;        NOW SUM 2'S COMPLEMENTED NEGATIVE SAMPLES
671     E5*:     MOV    B,C      ; FETCH NO OF SAMPLES
672              MVI    A,10Q    ; ADJUST BUFFER POINTER
673              SUB    B
674     E10*:    DCR    A
675              JM     E2*
676              INX    H
677              INX    H
678              JMP    E10*
679     E2*:     MOV    E,M      ; SAMPLES INTO D,E
680              INX    H
681              MOV    D,M
```

```
682              INX      H
683      ;       TAKE 2'S COMPLEMENT OF 9 BIT NUMBER
684      ;-IF (POSITIVE NUMBER) SKIP 2'S COMPLEMENT
685              MOV      A,D
686              ANI      2
687              CZ       TWCOMP
688      ;       AND STRIP SIGN BIT
689              MOV      A,D
690              ANI      1
691              MOV      D,A
692      ;-ENDIF
693              XTHL              ; PREVIOUS SUM INTO H,L
694              DAD      D
695              XTHL              ; ADDRESS POINTER INTO H,L
696              DCR      B
697              JNZ      E2@
698              POP      D        ; SUM INTO D,E
699      ; AVERAGE TOTAL
700      ;       DIVIDE BY 2
701      E3@:    XRA      A        ; CLEAR CARRY
702              MOV      A,D
703              RAR               ; SHIFT MS BYTE RIGHT INTO CARRY
704              MOV      D,A
705              MOV      A,E
706              RAR               ; SHIFT LS BYTE RIGHT, PICKING UP CARRY
707              MOV      E,A
708              XRA      A
709              MOV      A,C      ; SAMPLE COUNTER
710              RAR               ; DIVIDE BY 2
711              MOV      C,A
712              CPI      0
713              JNZ      E3@      ; DIVIDE AGAIN IF REQUIRED
714      ;       STORE AVERAGE IN VOLTAGE/RESISTANCE SAVE ADDRESS
715              XCHG              ; D,E INTO H,L
716              SHLD     PBCDVR
717              RET
718
```

ERR LINE            STATEMENT

```
719     SBTTL CAPACITANCE COMPENSATION ROUTINE
720     ;-------------------------------------------------------
721     ;
722     ;       INCREASE COMPENSATING CAPACITANCE
723     ;
724     ;       INPUT:
725     ;       CURRENT CAPACITANCE (CAPSAV)
726     ;
727     ;       OUTPUTS:
728     ;       CURRENT CAPACITANCE (CAPSAV)
729     ;       CARRY BIT (SET IF AT UPPER LIMIT ALREADY)
730     ;
731     ;-------------------------------------------------------
732     CAPINR:
733     ;-IF (MAXIMUM CAPACITANCE) THEN SET CARRY, RETURN
734             LDA      CAPSAV
735             CPI      374Q     ; 6 UPPER BITS LIMIT
```

```
736                 JNZ     @E10
737                 STC
738                 RET
739     ;-ELSE INCREMENT CAPACITANCE
740     ;--IF (BELOW LOWER CAP RANGE LIMIT)
741     @E10:       CPI     170
742                 JZ      @E30
743                 JNC     @E40
744     ;--THEN INCREMENT 1
745     @E20:       INR     A
746                 STA     CAPSAV
747                 OUT     CNPORT
748                 XRA     A           ; CLEAR CARRY
749                 RET
750     ;--ENDIF
751     ;--IF (AT LOWER CAP RANGE LIMIT)
752     ;--THEN SET HIGH RANGE, INCREMENT 1
753     @E30:       ORI     200Q        ; CX BIT (HIGH RANGE)
754                 JMP     @E20
755     ;--ENDIF
756     ; ALREADY IN HIGH RANGE - INCREMENT BY ADDING 4
757     @E40:       ADI     4Q
758                 STA     CAPSAV
759                 OUT     CNPORT
760                 RET
761     ;-ENDIF
762
763     SBTTL CORRECT COMPENSATION CHECK
764     ;---------------------------------------------------
765     ;
766     ; CHECK FOR CORRECT COMPENSATION DURING LAST 50%
767     ;       OF EACH CYCLE  AVERAGE OF READINGS MUST
768     ;       BE EQUAL TO OR GREATER THAN FINAL SET
769     ;       (+ AND -) READINGS
770     ;
771     ;       INPUT: NONE
772     ;
773     ;       OUTPUT: CARRY SET IF NOT CORRECT COMP
774     ;
775     ;---------------------------------------------------
776     COMPCK:
777     ; AVERAGE LAST SET OF READING (+ AND -)
778     ;       SAVE PREVIOUS COMPUTED AVERAGE
779                 LHLD    PBCDVR
780                 PUSH    H           ; SAVE ON TOP OF STACK
781                 MVI     B,1         ; NUMBER OF SAMPLES
782                 LXI     H,SAMPLE    ; DATA BUFFER POINTER
783                 CALL    AVE1
784                 LHLD    PBCDVR      ; FINAL READING AVERAGE
785                 XCHG                ;       INTO D,E
786                 POP     H           ; COMPUTED AVERAGE (LAST 50%)
787     ; COMPARE SUMMED AVERAGE WITH FINAL AVERAGE
788     ;       DON'T SAVE RESULT
789                 XRA     A           ; CLEAR CARRY
```

```
790             MOV     A,L         ; DOUBLE PRECISION SUBTRACT
791             SBB     E
792             MOV     A,H
793             SBB     D
794             JM      F10
795             XRA     A           ; COMPENSATED, CLEAR CARRY
796             RET
797     ;       RESULT NEGATIVE, NOT COMPENSATED
798     F10:    STC
799             RET
800
801     SBTTL CALIBRATE MODE PAUSE ROUTINE
802     ;----------------------------------------------------
803     ;       WAIT 2 SECONDS BEFORE BLANKING DISPLAY IN
804     ;                 CALIBRATE MODE
805     ;----------------------------------------------------
806     ;
807     CWAIT:  LXI     H,RATCON    ; RATE CONTROL POINTER
808             XRA     A           ; CLEAR COUNTER
809             MOV     M,A
810             INX     H
811             MOV     M,A
812     G10:    LDA     RATCON+1    ; MSB
813             CPI     140         ; 3K COUNT FOR 2 SEC INTRVL
814             JNZ     G10
815             RET                 ; TIMEOUT COMPLETE
816     ;
817     SBTTL VOLTAGE/RESISTANCE CONVERSION ROUTINE
818     ;----------------------------------------------------
819     ; ADC VOLTAGE TO RESISTANCE CONVERSION
820     ;       VIA TABLE LOOK-UP
821     ;----------------------------------------------------
822     VRCONV:
823     ; ADD (VOLTAGE READING X 2) TO RESISTANCE TABLE BASE ADDR
824     ;       TO CALCULATE TABLE ADDRESS OF RESISTANCE
825             LXI     H,VRTBL
826             XCHG                ; TABLE ADDRESS INTO D,E
827             LHLD    PBCDVR      ; VOLTAGE READING INTO H,L
828             DAD     H           ; VOLTAGE READING X 2
829             DAD     D           ; RESISTANCE ADDR NOW IN H,L
830             MOV     E,M         ; RESISTANCE INTO D,E
831             INX     H
832             MOV     D,M
833     ;-IF (CURRENT RANGE .EQ. 5 (RS=4M OHM))
834             LDA     RNGSAV
835             ANI     370
836             CPI     200         ; RANGE 5
837             JNZ     G100
838     ;-THEN MULTIPLY R IN D,E BY 4
839             XCHG                ; 16 BIT NUMBER IN H,L
840             DAD     H           ; X2
841             DAD     H           ; X2
842             XCHG                ; 4 X R NOW IN D,E
843     ; CONVERT BINARY NUMBER TO BCD
844     G100:   LXI     H,BCDBUF
845             CALL    BNBCD
846             RET
```

```
847     ;
848     SBTTL STATUS SWITCH SCAN
849     ;----------------------------------------------------
850     ;
851     ;        SCAN STATUS AND SWITCHES
852     ;
853     ;        OUTPUTS:
854     ;        CALIBRATE/NORMAL SW = CALIBRATE: CNFLAG 2ND MSB=1
855     ;        LOW VOLTAGE FLAG: CNFLAG MSB=1
856     ;        BATTERY READ REQUEST:  CARRY BIT SET
857     ;
858     ;----------------------------------------------------
859     STSCAN:
860     ; READ STATUS PORT BITS
861             IN      ADSTAT  ; CAL/NORM & LOW BATTERY FLAG
862             ANI     300Q    ; SAVE ONLY STATUS BITS
863             STA     CNFLAG
864     ; READ BATTERY CHECK SWITCH
865             IN      BATCK
866             RAL             ; PUT BIT INTO CARRY
867             RET
868     ;
869     SBTTL BATTERY LOW MESSAGE
870     ;----------------------------------------------------
871     ;       LOAD 'LLL' INTO DISPLAY BUFFER
872     ;----------------------------------------------------
873     ;
874     VLDISP: LXI     H,BCDBUF
875             MVI     A,377Q   ; BLANK
876             MOV     M,A
877             INX     H
878             MOV     M,A
879             INX     H
880             MVI     A,12Q    ; L
881             MVI     B,3
882     @G10:   MOV     M,A
883             INX     H
884             DCR     B
885             JNZ     @G10
886     ; RETURN DISPLAY POINTER TO H,L
887             LXI     H,BCDBUF
888             RET
889
890     SBTTL DISPLAY DRIVER
891     ;----------------------------------------------------
892     ;
893     ; DISPLAY CONTENTS OF BCDBUF BASED ON
894     ;       RESISTANCE RANGE AND STATUS DATA
895     ;
896     ;       INPUT: H,L POINTS TO BCDBUF (MSD)
897     ;
898     ;----------------------------------------------------
899     DISPLY:
900     ;-IF (MSB .EQ. 377) THEN MESSAGE TO BE OUTPUT
901     ;       OUTPUT MESSAGE IN LIEU OF DATA
902             MOV     A,M
903             CPI     377Q
904             JNZ     @@G10
```

```
905             OUT     DISPM
906             INX     H
907             INX     H
908             MOV     A,M
909             OUT     DISP3
910             INX     H
911             MOV     A,M
912             OUT     DISP2
913             INX     H
914             MOV     A,M
915             OUT     DISPL
916             RET
917     ;-ELSE DATA IS PRESENT FOR OUTPUT
918     ; DETERMINE CURRENT RESISTANCE RANGE (1 THRU 5)
919     ..G10:  XRA     A
920             MOV     B,A     ; CLEAR RANGE REGISTER, B
921             LDA     RNGSAV
922     ..G20:  INR     B
923             RAR
924             JNC     ..G20
925     ;-ENDIF
926     ;-IF (MEASURED R .LT. R SERIES REFERENCE)
927             INX     H       ; GET RESISTANCE MSD (4TH OF 4)
928             MOV     A,M
929             CPI     0
930             JNZ     ..G100
931             JMP     ..G30
932     ;-THEN MULTIPLIER .EQ. RANGE-1
933     ; SUBTRACT 1 FROM RANGE AND OUTPUT TO MULTIPLIER DISPLAY DIGIT
934     ..G30:  MOV     A,B
935             DCR     A
936     ;--IF (MULTIPLIER .EQ. 0) THEN BLANK DISPLAY DIGIT
937             JNZ     ..G40
938             MVI     A,377Q
939             OUT     DISPM
940     ;--ELSE OUTPUT MULTIPLIER
941     ..G40:  OUT     DISPM
942     ;--ENDIF
943     ;-ENDIF
944     ; OUTPUT 3 RESISTANCE DIGITS
945     ;-IF (MSD OF 3 .EQ. 0) THEN SUPPRESS LEADING ZERO
946             INX     H
947             MOV     A,M
948             CPI     0
949             JNZ     ..G50
950             MVI     A,377Q  ; BLANK
951             OUT     DISP3
952             JMP     ..G60
953     ;-ELSE OUTPUT DIGIT
954     ..G50:  OUT     DISP3
955     ;-ENDIF
956     ;       OUTPUT 2 REMAINING DIGITS
957     ..G60:  INX     H
958             MOV     A,M
959             OUT     DISP2
960             INX     H
961             MOV     A,M
962             OUT     DISPL
963             RET
964     ; FOR MEASURED R .GE. R SERIES REFERENCE -
965     ;       OUTPUT RANGE MULTIPLIER AND UPPER 3 DIGITS OF 4
```

```
966     ;          (H,L CURRENTLY POINTING TO MSD)
967     ..G10.: MOV     A,B       ; RANGE
968     ;-IF (RANGE .EQ. 5) THEN DECREMENT RANGE
969             CPI     5
970             JNZ     ..G150
971             DCR     A
972     ;.ENDIF
973     ..G150: OUT     DISPM
974             MOV     A,M
975             OUT     DISP3
976             INX     H
977             MOV     A,M
978             OUT     DISP2
979             INX     H
980             MOV     A,M
981             OUT     DISPL
982             RET
983
984     SBTTL BATTERY VOLTAGE READ/DISPLAY
985     ;===========================================================
986     ;          READ AND DISPLAY BATTERY VOLTAGE
987     ;===========================================================
988     BVSCAN: NOP
989             CALL    CONVRD    ; READ BATTERY VLTAGE/35
990     ;                          STORE IN D,E TEMP
991     ; CALCULATE TABLE ADDRESS WHERE BASE VOLTAGE
992     ;       IS 3.125V X 3.5=10.94V (ADC READS D320)
993             LXI     B,320
994             XRA     A         ; CLEAR CARRY
995     ;       SUBTRACT TABLE BASE (320) FROM ADC
996     ;               VOLTAGE READING
997             MOV     A,E       ; BATTERY VOLTAGE, 8 LSB
998             SBB     C         ; BASE OF INTEREST IN C
999     ;       MULTIPLY BY 2 SINCE 2 BYTES PER WORD
1000            ANI     177Q      ; CLEAR MSB
1001            RLC
1002    ;-IF (OFFSET PAST END OF TABLE) THEN OUTPUT 'HI' MESS
1003            CPI     150
1004            JM      .AG10
1005            CALL    HI
1006            STC
1007            RET
1008    ;.ENDIF
1009    ;       ADD CALCULATED OFFSET TO START OF TABLE
1010    .AG10:  MOV     E,A       ; OFFSET IN D,E
1011            XRA     A
1012            MOV     D,A
1013            LXI     H,BVTBL   ; TABLE POINTER
1014            DAD     D         ; ACTUAL BATTERY VOLTAGE ADDR POINTER
1015            MOV     E,M       ; BATTERY VLTAGE INTO D,E
1016            INX     H
1017            MOV     D,M
1018    ; CONVERT BATTERY VOLTAGE FROM BINARY TO BCD
1019            LXI     H,BCDBUF
1020            CALL    BNBCD
1021            XRA     A         ; CLEAR CARRY
1022            RET
1023    ;
1024    SBTTL OUT OF RANGE 'HI' MESSAGE
1025    ;===========================================================
1026    ; LOAD 'HI' INTO DISPLAY BUFFER
1027    ;===========================================================
```

```
1028  HI:     LXI     H,BCDBUF
1029          MVI     A,3770    ; BLANK
1030          MVI     B,3
1031  @AH10:  MOV     M,A
1032          INX     H
1033          DCR     B
1034          JNZ     @AH10
1035          MVI     A,130     ; H
1036          MOV     M,A
1037          INX     H
1038          MVI     A,1       ; I
1039          MOV     M,A
1040  ; RETURN DISPLAY POINTER TO H,L
1041          LXI     H,BCDBUF
1042          RET
1043  ;
1044
1045
1046  SBTTL 16 BIT BINARY TO BCD CONVERSION
1047  ;-----------------------------------------------------------
1048  ;
1049  ;       16 BIT BINARY TO BCD CONVERSION
1050  ;
1051  ;       INPUTS:
1052  ;       UNSIGNED BINARY NUMBER IN D,E
1053  ;       BCD BUFFER POINTER IN H,L (BCDBUF)
1054  ;
1055  ;       OUTPUT:
1056  ;       5 BCD DIGITS, ONE PER BYTE
1057  ;       H,L POINTS TO MSD IN FIRST LOCATION
1058  ;
1059  ;-----------------------------------------------------------
1060  BNBCD:  PUSH    PSW       ; SAVE VARIABLES
1061          PUSH    B
1062          PUSH    D
1063          PUSH    H
1064          XCHG              ; BINARY NO IN HL, ADDR IN DE
1065          LXI     B,-10000
1066          CALL    I1@       ; GET MSD
1067          LXI     B,-1000
1068          CALL    I1@
1069          LXI     B,-100
1070          CALL    I1@
1071          LXI     B,-10
1072          CALL    I1@
1073          MOV     A,L       ; GET LSD
1074          STAX    D         ; STORE IT
1075          POP     H
1076          POP     D
1077          POP     B
1078          POP     PSW
1079          RET
1080  ; BCD NUMBER
1081  I1@:    XRA     A         ; A=0 USE 30H FOR ASCII
1082          PUSH    D         ; SAVE ADDRESS
1083  I2@:    MOV     E,L       ; SAVE BINARY
1084          MOV     D,H
1085          INR     A         ; INCREMENT DIGIT
```

```
1086            DAD     B       ; SUBTRACT
1087            JC      I20     ; RESULT NEGATIVE?
1088            DCR     A       ; YES, RESTORE DIGIT COUNT
1089            MOV     L,E     ; BINARY NUMBER TO H,L
1090            MOV     H,D
1091            POP     D       ; GET ADDRESS
1092            STAX    D       ; STORE DIGIT
1093            INX     D       ; INCREMENT POINTER
1094            RET
1095
1096    SBTTL LOOK-UP TABLES
1097            ORG     40000   ; EPROM FOR LOOK-UP TABLES
1098    ;       CONVERT BCD WORDS TO HEX BYTES, LSB FIRST
1099    ;-----------------------------------------------------
1100    ; VOLTAGE TO RESISTANCE CONVERSION TABLE
1101    ;       RANGE INCLUDES ZERO TO R REF X 5
1102    ;-----------------------------------------------------
1103    VRTBL:
1104            DW      0,2,4,6,8
1105            DW      10,12,14,16,18
1106            DW      20,22,24,26,28
1107            DW      30,32,34,36,39
1108            DW      41,43,45,47,49
1109            DW      51,54,56,58,60
1110            DW      62,65,57,69,71
1111            DW      73,76,78,80,82
1112            DW      85,87,89,92,94
1113            DW      96,99,101,103,106
1114            DW      108,111,113,115,118
1115            DW      120,123,125,128,130
1116            DW      133,135,138,140,143
1117            DW      145,148,151,153,156
1118            DW      158,161,164,166,169
1119            DW      172,174,177,180,182
1120            DW      185,188,191,193,196
1121            DW      199,202,205,208,210
1122            DW      213,216,219,222,225
1123            DW      228,231,234,237,240
```

| | | |
|---|---|---|
| 1124 | DW | 243,246,249,252,255 |
| 1125 | DW | 258,261,264,267,270 |
| 1126 | DW | 274,277,280,283,286 |
| 1127 | DW | 290,293,296,300,303 |
| 1128 | DW | 306,309,313,316,320 |
| 1129 | DW | 323,326,330,333,337 |
| 1130 | DW | 340,344,347,351,355 |
| 1131 | DW | 358,362,365,369,373 |
| 1132 | DW | 376,380,384,388,391 |
| 1133 | DW | 395,399,403,407,410 |
| 1134 | DW | 414,418,433,426,430 |
| 1135 | DW | 434,438,442,446,450 |
| 1136 | DW | 454,459,463,467,471 |
| 1137 | DW | 475,480,484,488,493 |
| 1138 | DW | 497,501,505,510,515 |
| 1139 | DW | 519,524,528,533,538 |
| 1140 | DW | 542,547,552,556,561 |
| 1141 | DW | 566,571,575,580,585 |
| 1142 | DW | 590,595,600,605,610 |
| 1143 | DW | 615,620,625,630,635 |
| 1144 | DW | 641,646,652,657,662 |
| 1145 | DW | 668,673,679,684,690 |
| 1146 | DW | 695,701,707,712,718 |
| 1147 | DW | 724,730,736,742,747 |
| 1148 | DW | 753,760,766,772,778 |
| 1149 | DW | 784,790,797,803,809 |
| 1150 | DW | 816,822,829,835,842 |
| 1151 | DW | 848,855,861,869,876 |
| 1152 | DW | 882,889,896,903,911 |

| | | |
|---|---|---|
| 1153 | DW | 918,925,932,939,947 |
| 1154 | DW | 954,962,969,977,985 |
| 1155 | DW | 992,1000,1010,1020,1024 |
| 1156 | DW | 1032,1040,1050,1060,1065 |
| 1157 | DW | 1073,1081,1090,1100,1110 |
| 1158 | DW | 1120,1125,1133,1142,1151 |
| 1159 | DW | 1160,1170,1180,1190,1200 |
| 1160 | DW | 1210,1220,1230,1240,1250 |
| 1161 | DW | 1260,1270,1280,1290,1300 |
| 1162 | DW | 1310,1320,1330,1340,1350 |
| 1163 | DW | 1360,1371,1382,1393,1404 |
| 1164 | DW | 1415,1430,1440,1450,1462 |
| 1165 | DW | 1474,1490,1500,1510,1522 |
| 1166 | DW | 1535,1550,1560,1573,1590 |
| 1167 | DW | 1600,1612,1625,1640,1653 |
| 1168 | DW | 1670,1681,1695,1710,1724 |
| 1169 | DW | 1740,1753,1770,1783,1800 |
| 1170 | DW | 1813,1830,1845,1861,1880 |
| 1171 | DW | 1893,1910,1926,1943,1960 |
| 1172 | DW | 1980,1994,2012,2030,2050 |
| 1173 | DW | 2070,2084,2103,2122,2141 |
| 1174 | DW | 2161,2180,2200,2220,2241 |
| 1175 | DW | 2261,2282,2304,2325,2350 |
| 1176 | DW | 2370,2391,2414,2440,2460 |
| 1177 | DW | 2483,2510,2531,2555,2581 |
| 1178 | DW | 2610,2632,2660,2684,2711 |
| 1179 | DW | 2740,2765,2793,2821,2850 |
| 1180 | DW | 2880,2910,2940,2670,3001 |
| 1181 | DW | 3032,3064,3100,3130,3163 |

```
1182            DW      3200,3230,3270,3303,3340
1183            DW      3380,3414,3453,3492,3532
1184            DW      3572,3613,3660,3700,3742
1185            DW      3790,3831,3880,3924,3972
1186            DW      4020,4070,4121,4173,4230
1187            DW      4280,4334,4390,4450,4510
1188            DW      4570,4630,4690,4754,4820
1189            DW      4890,4955,5025,5100,5170
1190
1191    ;----------------------------------------------------
1192    ;
1193    ; ADC VOLTAGE TO BATTERY VOLTAGE CONVERSION TABLE
1194    ;       RANGE INCLUDES 10.9V TO 13.5V DC
1195    ;
1196    ;       OUTSIDE THIS BOUNDARY RESULTS IN ERROR MESSAGE
1197    ;
1198    ;----------------------------------------------------
1199    BVTBL:
1200            DW      109,110,110,110,111
1201            DW      111,111,112,112,112
1202            DW      113,113,113,114,114
1203            DW      114,115,115,116,116
1204            DW      116,117,117,117,118
1205            DW      118,118,119,119,119
1206            DW      120,120,120,121,121
1207            DW      121,122,122,122,123
1208            DW      123,123,124,124,124
1209            DW      125,125,125,126,126
1210            DW      126,127,127,127,128
1211            DW      128,129,129,129,130
1212            DW      130,130,131,131,131
1213            DW      132,132,132,133,133
1214            DW      133,134,134,134,135
```

```
1215    ;
1216
1217    SBTTL VARIABLES
1218    ;
1219            ORG       1010OQ
1220    RAMSTART        EQU     $
1221    ;
1222    ; RATE CONTROL COUNTER (INTERRUPT DRIVEN)
1223    RATCON: DS      2
1224    ; RESISTANCE RANGE, A/D CONVERT CMD, EXCITATION SAVE
1225    RNGSAV: DS      1
1226    ; DISPLAY BUFFER (MSD FIRST)
1227    BCDBUF: DS      5
1228    ; CALIBRATE/NORMAL SW & LOW VOLTAGE FLAG
1229    CNFLAG: DS      1           ; CAL: 2ND MSB=1
1230    ;                           ; VLOW:  MSB=1
1231    ; PACKED BCD VOLTAGE/RESISTANCE DATA
1232    PBCDVR: DS      2
1233    ; 50/100 HZ INDICATOR (2 LS BITS)
1234    INCR12: DS      1           ; 50HZ=2, 100HZ=1
1235    ; COMPENSATION SAVE
1236    CAPSAV: DS      1
1237    ; SAMPLE SAVE AREA (16 SAMPLES X 2 BYTES/SAMPLE)
1238    SAMPLE: DS      40Q
1239    ; PROCESSOR SLEEP STATE ADDRESS
1240    SLEEP:  DS      1
1241    RAMEND  EQU     $
1242
1243    SBTTL CONSTANTS
1244    ;
1245    ; BLANK & CONVERT* COMMAND (ADC) PORT BIT
1246    ADCONV  EQU     40Q
1247    ; PLUS EXCITATION VOLTAGE (4990V)
1248    DAPLUS  EQU     300Q
1249    ; ZERO EXCITATION VOLTAGE
1250    DAZERO  EQU     200Q
1251    ; STROBE RANGE, A/D CONVERT CMD, EXCITATION PORT
1252    RNPORT  EQU     44Q
1253    ; STROBE CAPACITANCE COMPENSTATION PORT
1254    CNPORT  EQU     45Q
1255    ; STROBE ADC INPUT PORT (8-LSB)
1256    ADCLS   EQU     40Q
1257    ; STROBE ADC (2 MS BITS), STATUS INPUT PORT
1258    ADSTAT  EQU     41Q
1259    ; STROBE DISPLAY (MULTIPLIER DIGIT)
1260    DISPM   EQU     40Q
1261    ; STROBE DISPLAY (MSD)
1262    DISP3   EQU     43Q
1263    ; STROBE DISPLAY (2ND DIGIT)
1264    DISP2   EQU     42Q
1265    ; STROBE DISPLAY (LSD)
1266    DISPL   EQU     41Q
1267    ; STROBE BATTERY CHECK INPUT PORT
1268    BATCK   EQU     42Q
1269    ;
1270    END
```

SYMBOL TABLE LIST

| SYMBOL | VALUE | TYPE | SEGMENT | SYMBOL | VALUE | TYPE | SEGMENT |
|---|---|---|---|---|---|---|---|
| $ | 0000 | ADDR | MAIN | A22* | 01C7 | ADDR | MAIN |
| **G10* | 0491 | ADDR | MAIN | A30* | 01CB | ADDR | MAIN |
| **G15* | 049A | ADDR | MAIN | A31* | 01E9 | ADDR | MAIN |
| **G1* | 0459 | ADDR | MAIN | A32* | 01F2 | ADDR | MAIN |
| **G2* | 045E | ADDR | MAIN | A33* | 01FC | ADDR | MAIN |
| **G3* | 046D | ADDR | MAIN | A34* | 0205 | ADDR | MAIN |
| **G4* | 0476 | ADDR | MAIN | A3* | 00E7 | ADDR | MAIN |
| **G5* | 0486 | ADDR | MAIN | A40* | 0209 | ADDR | MAIN |
| **G6* | 048A | ADDR | MAIN | A41* | 0227 | ADDR | MAIN |
| *A10* | 004F | ADDR | MAIN | A42* | 0230 | ADDR | MAIN |
| *A1* | 008A | ADDR | MAIN | A43* | 0234 | ADDR | MAIN |
| *A2* | 009C | ADDR | MAIN | A44* | 0243 | ADDR | MAIN |
| *A5* | 009F | ADDR | MAIN | A4* | 010A | ADDR | MAIN |
| *AG1* | 04BD | ADDR | MAIN | A50* | 0247 | ADDR | MAIN |
| *AH1* | 04D6 | ADDR | MAIN | A51* | 0260 | ADDR | MAIN |
| *E1* | 03B6 | ADDR | MAIN | A52* | 0264 | ADDR | MAIN |
| *E2* | 03BE | ADDR | MAIN | A53* | 026E | ADDR | MAIN |
| *E3* | 03C6 | ADDR | MAIN | A54* | 0277 | ADDR | MAIN |
| *E4* | 03CB | ADDR | MAIN | A5* | 0116 | ADDR | MAIN |
| *G1* | 0439 | ADDR | MAIN | A6* | 0121 | ADDR | MAIN |
| A | 0007 | REG | MAIN | ADCLB | 0020 | CNST | MAIN |
| A10* | 0124 | ADDR | MAIN | ADCONV | 0020 | CNST | MAIN |
| A11* | 012D | ADDR | MAIN | ADSTAT | 0021 | CNST | MAIN |
| A12* | 0159 | ADDR | MAIN | AVE1 | 033F | ADDR | MAIN |
| A13* | 0167 | ADDR | MAIN | B | 0000 | REG | MAIN |
| A14* | 016A | ADDR | MAIN | B1* | 02A9 | ADDR | MAIN |
| A15* | 019F | ADDR | MAIN | BATCH | 0022 | CNST | MAIN |
| A16* | 01A2 | ADDR | MAIN | BCDBUF | 1043 | ADDR | MAIN |
| A17* | 0194 | ADDR | MAIN | BFGIN | 0049 | ADDR | MAIN |
| A1* | 00D6 | ADDR | MAIN | BNBCD | 04E7 | ADDR | MAIN |
| A20* | 01A6 | ADDR | MAIN | BVSCAN | 04A6 | ADDR | MAIN |
| A21* | 01C4 | ADDR | MAIN | BVTBL | 085C | ADDR | MAIN |

0 ERROR(S) IN PROGRAM
128 SYMBOLS IN PROGRAM

The embodiments of the invention in which an exclusive property or privilege is claimed are defined as follows:

1. An instrument for measuring the impedance of an electrical device through a transmission line having one end connected to said electrical device and the other end connected to said instrument comprising:

signal generating means for generating an excitation signal having a particular wave shape;

compensation circuit means for compensating for the capacitance of the transmission line coupled between said signal generating means and said other end of the transmission line, said compensation circuit means, the transmission line, and said electrical device being responsive to said excitation signal to develop an output signal at the other end of the transmission line corresponding to the voltage across the transmission line and said electrical device; and signal processing means coupled to said other end of the transmission line for sampling said output signal and comparing the wave shape of the said signal with said particular wave shape, said signal processing means further being connected to said compensation circuit means and acting to control the impedance of said compensation circuit means to bring the wave shape of the output signal within a preselected correspondence with said particular wave shape wherein the output signal is indicative of the impedance of the transmission line and the device.

2. The instrument of claim 1 wherein said signal processing means further acts to measure said sampled output signal for calculating the impedance of the device.

3. The instrument of claim 2 further comprising delay means coupled to said signal processing means for displaying said calculated impedance.

4. The instrument of claim 1 further comprising range select means including a plurality of resistors connected in parallel with said compensation circuit means for limiting the amplitude of the output signal, said signal processing means further being connected to said range select means and acting to control said range select means wherein an appropriate resistor range is selected to bring the amplitude of the output signal within a preselected value.

5. The instrument of claim 4 wherein said compensating circuit means comprises a plurality of capacitors and a plurality of switching devices, each associated with a different one of said capacitors and each individually operable by said signal processing means.

6. The instrument of claim 5 wherein said capacitors are binary weighted in value.

7. The instrument of claim 4 wherein said range select means comprises a plurality of resistors and a plurality of switching devices, each associated with a different one of said resistors and each individually operable by said signal processing means.

8. The instrument of claim 7 further comprising an additional range resistor connected between said signal generating means and said range select means.

9. The instrument of claim 8 wherein said signal generating means comprises a microprocessor.

10. The instrument of claim 8 wherein said particular wave shape is a bipolar square wave.

11. The instrument of claim 10 wherein said preselected value is 50% to 90% of the amplitude of the excitation signal.

12. The instrument of claim 11 wherein said signal processing means further comprises timing means for generating a timing signal which establishes the frequency of the excitation signal and which establishes output signal sampling rates.

13. The instrument of claim 12 wherein the output signal is sampled near the leading and trailing edges of the positive and negative half cycles of the bipolar square wave signal.

14. The instrument of claim 13 wherein said signal processing means averages the signal samples for a plurality of cycles of the excitation signal.

15. The instrument of claim 14 wherein the frequency of the excitation signal is 50 Hz.

16. The instrument of claim 1 wherein the instrument power source is a battery.

* * * * *